(12) United States Patent
Hurley

(10) Patent No.: US 7,001,588 B2
(45) Date of Patent: Feb. 21, 2006

(54) EXPANDED PORPHYRIN COMPOSITIONS FOR TUMOR INHIBITION

(75) Inventor: Laurence H. Hurley, Tucson, AZ (US)

(73) Assignee: Cylene Pharmaceuticals, San Diego, CA (US)

( * ) Notice: Subject to any disclaimer, the term of this patent is extended or adjusted under 35 U.S.C. 154(b) by 4 days.

(21) Appl. No.: 10/661,241

(22) Filed: Sep. 12, 2003

(65) Prior Publication Data

US 2004/0110820 A1 Jun. 10, 2004

Related U.S. Application Data

(60) Provisional application No. 60/460,534, filed on Apr. 4, 2003, provisional application No. 60/410,475, filed on Sep. 12, 2002.

(51) Int. Cl.
*A61B 5/55* (2006.01)
*A61B 10/00* (2006.01)
*C07B 47/00* (2006.01)
*C07F 5/10* (2006.01)
*A61K 31/40* (2006.01)

(52) U.S. Cl. ............ 424/9.362; 540/145; 534/15; 514/185; 514/410; 424/9.1; 424/9.61

(58) Field of Classification Search .......... 540/145; 534/15; 514/185, 410; 424/9.1, 9.61, 9.362
See application file for complete search history.

(56) References Cited

OTHER PUBLICATIONS

Narayanan et al. Interaction of RH(I) with meso-Arylsapphyrinsa and -Rubyrins: First Structural Characterization of Bimetallic Hetero-rubyrin Complex. Feb. 21, 2001, Inorg. Chem. 2001, 40, pp. 1637-1645.*
Narayanan et al. Novel Core-Modified Expanded Porphyrins with meso-Aryl Sustituents: Syhtesis, Spectral and Structural Characterization. Sep. 21, 1999, J. Am. Chem. Soc. 1999, 121, pp. 9053-9068.*
Foye et al. Principles of Medicinal Chemistry. 1995. Williams & Wilkins. Fourth Edition. pp. 902-907.*
Goldman et al. Cecil Textbook of Medicine. 2000. W.B. Saunders Company. Twenty-First Edition. p. 558.*
Narayanan et al. Interaction of Rh(I) with meso-arylsapphyrins and -Rubyrins: First Structural Characterization of Bimetallic Hetero-rubyrin Complex. Inorg Chem. 2001, 40, pp. 1637-1645.*
Narayanan et al. Novel Core-Modified Expanded Porphyrins with meso-Aryl Substituents: Synthesis, Spectral and Structural Chracterization. J. Am. Chem. Soc. 1999, 121. pp. 9053-9068.*
Hilmey et al., J. Med. Chem. (2002) 45:449-461.
Stilts et al., J. Med. Chem. (2000) 43:2403-2410.

* cited by examiner

*Primary Examiner*—James O. Wilson
*Assistant Examiner*—Matthew L. Fedowitz
(74) *Attorney, Agent, or Firm*—Morrison & Foerster LLP

(57) ABSTRACT

Expanded porphyrin comprising substitutions for at least two NH groups by S, Se or Te are non-photoactive and are selective for binding G-quadruplexes characteristic of the c-MYC control region. Accordingly, these expanded porphyrins are useful to modulate the expression of genes controlled by the formation of c-MYC type G-quadruplexes, such as c-MYC itself.

6 Claims, 8 Drawing Sheets

Se2SAP

EXPANDED PORPHYRIN COMPOSITIONS FOR TUMOR INHIBITION

CROSS-REFERENCE TO RELATED APPLICATIONS

This application claims priority under 35 U.S.C. § 119(e) from U.S. Ser. No. 60/460,534 filed 4 Apr. 2003 and U.S. Ser. No. 60/410,475 filed 12 Sep. 2002. The contents of these documents are incorporated herein by reference.

This invention was made in part with government support under Grant Nos. CA88310 and CA94166 awarded by the National Institutes of Health. The government has certain rights in this invention.

TECHNICAL FIELD

The invention relates to compounds that inhibit c-MYC expression by binding the G-quadruplex formed in the control region of that gene. More specifically, the invention relates to expanded porphyrins that are rendered non-photoactive and that contain S or Se atoms positioned to interact selectively with G-quadruplexes of the conformation characterizing the c-MYC gene.

BACKGROUND ART

The emerging evidence for the involvement of G-quadruplex structures in cellular processes such as transcription control of c-MYC has stimulated the development of drugs that have selectivity between different G-quadruplex structures. G-quadruplexes are intramolecular complexes formed in the presence of large numbers of guanines in a small region of DNA. The promoter regions of some important genes such as the insulin, c-MYC, PDGF, HER-2/neu, and c-MYB genes, human and chicken β-globin genes, rat preproinsulin II gene, adenovirus serotype 2 and retinoblastoma susceptibility genes have been found to contain G-rich sequences that have the ability to form G-quadruplex structures under physiological conditions. To date, the involvement of these quadruplex structures in transcription control has been shown only for the insulin gene and the c-MYC gene. Due to the structural polymorphism in G-quadruplex structures, different G-quadruplex topologies are associated with different signaling pathways.

There are at least three proposed conformations of G-quadruplexes. These are basket type, propeller type, and chair type. (See FIGS. 1A–1C.) One type G-quadruplex structures is believed to be present in the human telomeric sequence and inhibits telomerase activity by sequestration of the substrate required for enzyme activity. (Telomerase is involved in telomere maintenance in tumor cells; inhibition leads to the telomere shortening and senescence.)

On the other hand, another type G-quadruplex is found in the control regions of the c-MYC gene and the formation of this type of G-quadruplex inhibits transcription. This is significant because overexpression of c-MYC results in increased cellular proliferation in many malignancies including breast, colon, cervix, small cell lung cancer, osteosarcomas, glioblastomas and myeloid leukemias. The nuclease hypersensitivity element (NHE) III$_1$ upstream of the P1 promoter of c-MYC controls up to 85–90% of the transcriptional activation of this gene.

It has been shown that c-MYC transcription can be controlled by stabilizing the relevant G-quadruplex through interaction with the cationic porphyrin TMPyP4. (FIG. 2A.) TMPyP4 stabilizes the G-quadruplex structure with some, but far from perfect, selectivity.

Various cationic porphyrins bind to and stabilize different types of G-quadruplexes, and in some cases facilitate G-quadruplex formation. TMPyP4 also associates with the intramolecular G-quadruplex formed in the human telomeric sequence and this association results in telomerase inhibition. It would be desirable to develop drugs that can differentiate between different types of G-quadruplexes structures for achieving therapeutic selectivity.

Another goal is to provide compounds that associate with G-quadruplexes but which lack the photoinduced cytotoxicity of the porphyrins. It has been shown that substituting selenium for nitrogen in the porphyrin core can eliminate this photocytotoxicity. See Stilts, C. E., et al., *J. Med. Chem.* (2000) 43:2403–2410 and Hilmey, D. G., et al., *J. Med. Chem.* (2002) 45:449–461.

The invention is designed to provide non-photocytotoxic compounds that associate selectively with the type of G-quadruplex that characterizes c-MYC.

DISCLOSURE OF THE INVENTION

The invention provides compounds that are non-photocytotoxic forms of expanded porphyrins that selectively bind the type of G-quadruplex structure found in the promoter region of the c-MYC gene. The compounds are expanded porphyrin analogs which contain at least two selenium, tellurium or sulfur atoms substituted for nitrogen, spaced so as to interact with carbonyl groups in quadruplexed guanines, and which contain at least five pyrrole moieties or mimics thereof cyclized to obtain a macrocycle. The pyrrole or pyrrole mimics may further be substituted by alkyl groups, and one or more carbons in pyrrole or pyrrole mimics may be replaced by O or S.

Thus, in one aspect, the invention is directed to expanded porphyrin analogs that selectively interact with G-quadruplexes of the type associated with c-MYC, which expanded porphyrins comprise at least five pyrrole moieties or open chain mimics thereof, cyclized through a bond or alkylene bridge between said pyrroles or pyrrole mimics; wherein said bridge may optionally be included in an aromatic ring system, and wherein at least one carbon in each alkylene or alkenylene bridge is substituted by a cation containing or cation forming moiety (R$^1$) and at least two pyrrole or pyrrole-mimic nitrogens are replaced by Se, Te or S; and wherein said pyrrole or pyrrole mimics may optionally be substituted with lower alkyl (1–4C); and wherein one or more carbons of the pyrrole or pyrrole mimic may be replaced by O or S.

Illustrative of the compounds of the invention are those of formulas

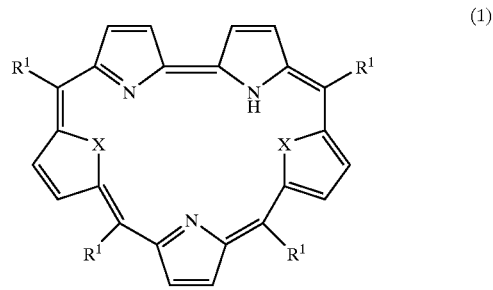

(1)

-continued
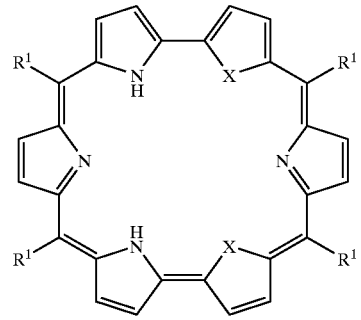
(2)
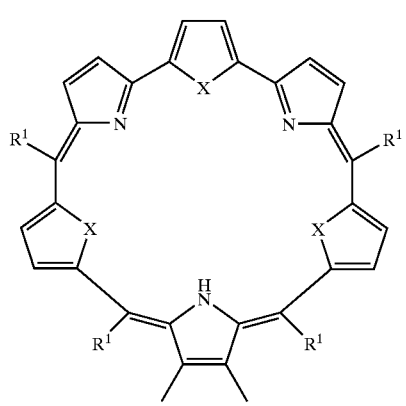
(3)
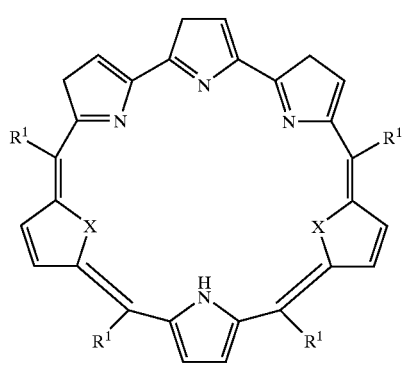
(4)
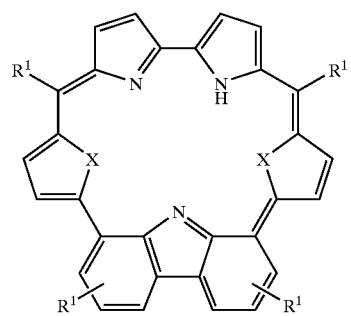
(5)
-continued
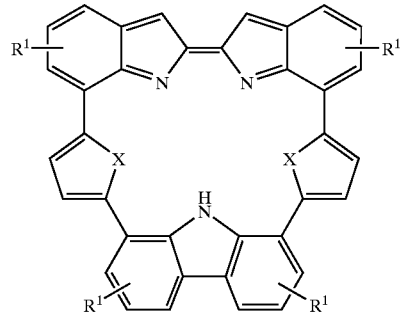
(6)
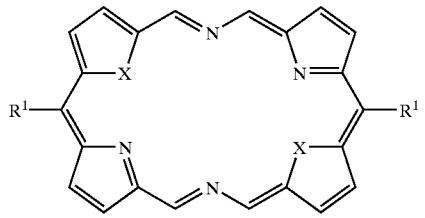
(7)
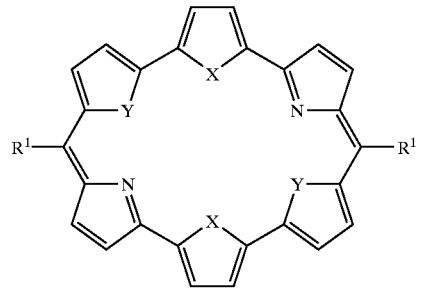
(8)
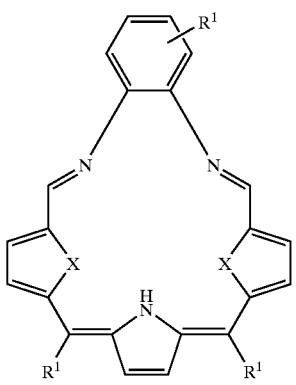
(9)
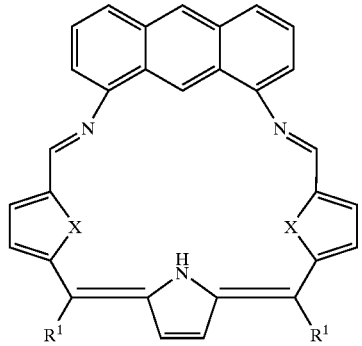
(10)

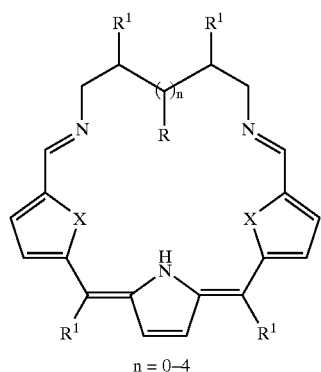
(11)
n = 0–4
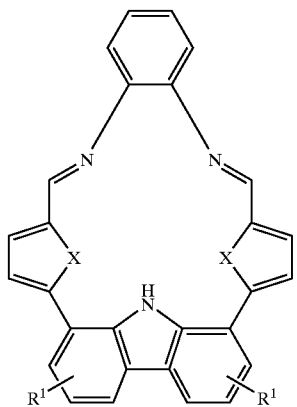
(15)
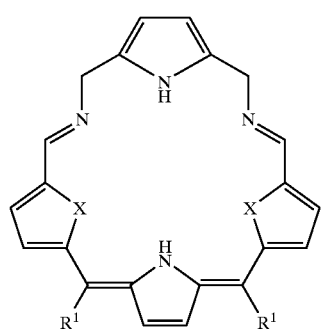
(12)
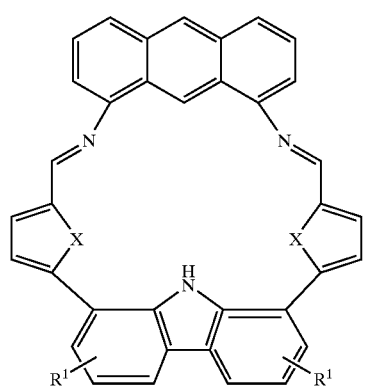
(16)
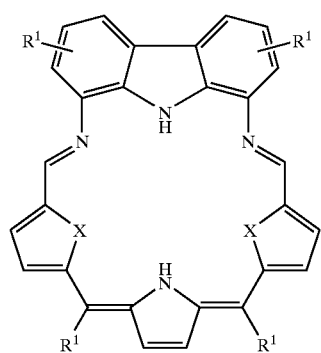
(13)
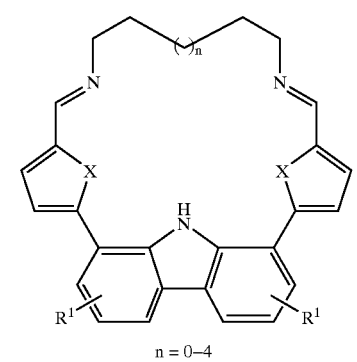
(17)
n = 0–4
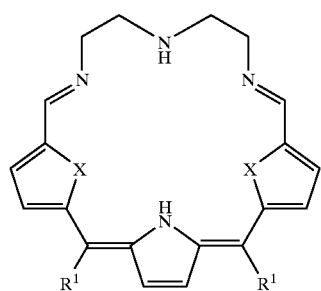
(14)
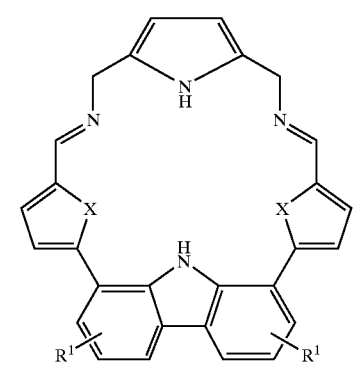
(18)

-continued (19)

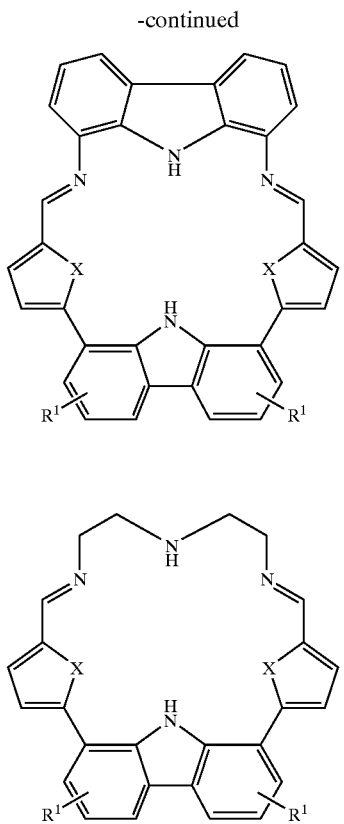

(20)

wherein each X is S, Se or Te. Additional NH components of the pyrrole or pyrrole mimics may be replaced by S, Se or Te. Each $R^1$ is H, an aryl group, alkyl (1–6C), alkenyl (2–6C) optionally comprising a cation containing or forming substituent; the pyrrole and phenyl moieties may optionally be substituted by one or more lower alkyl (1–4C) groups; and one or more carbons in each pyrrole or phenyl moiety may be replaced by O or S. At least one $R^1$ must contain a cation or cation-forming group.

The formulas (1)–(20) above show typical locations for $R^1$; however $R^1$ may be present at other locations as well as at any location not a member of the pyrrole or pyrrole mimic. For example, in formula (16), $R^1$ may be present in the anthrocene moiety. More than one $R^1$ may be substituted on an aryl group.

Typical cationic-containing substituents include

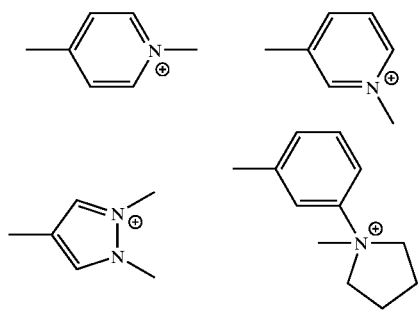

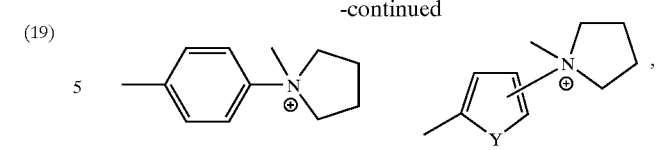

wherein Y is NH, S, Se or O. The substituents may also be amines generally such as $(CH_2)_xNR_2$ or $(CH_2)_xNR^+_3$ wherein each R is H or alkyl.

In another aspect, the invention is directed to methods to inhibit tumor growth by contacting tumor cells with the compounds of the invention. Said contacting may be in vivo or in vitro; accordingly, another aspect of the invention comprises pharmaceutical and veterinary compositions containing the compounds of the invention and methods to use these compositions to treat human and other animal subjects.

BRIEF DESCRIPTION OF THE DRAWINGS

FIG. 1A shows chair type. FIG. 1B shows basket type. FIG. 1C shows propeller type.

FIG. 4A shows the results with respect to the c-MYC G-quadruplex and FIG. 4B shows the results with respect to the telomeric G-quadruplex.

FIG. 5A shows the results with respect to the c-MYC G-quadruplex and FIG. 5B shows the results with respect to the telomeric G-quadruplex.

MODES OF CARRYING OUT THE INVENTION

The invention relates to compounds that selectively target type of G-quadruplex complexes characteristic of c-MYC and thus are useful in the treatment of malignancies. By "treatment" is meant improvement in the condition of a subject, not necessarily a complete cure or complete prevention. "Treatment" also includes prophylaxis; again, it is not expected that each and every subject treated will avoid malignancy; rather the probability that malignancy will occur is decreased. Similarly, in a therapeutic mode, it is not expected that every subject will be completely recovered; however, in a substantial number of cases, an extension of lifespan and/or improvement of life quality are achieved.

The tumors that are susceptible to treatment with the compounds of the invention are those mediated by the expression of c-MYC wherein the transcription from this gene is regulated by a G-quadruplex. Because the compounds of the invention are able to interrupt transcription due to their association with the G-quadruplex, they are useful in the treatment of these conditions. Further, the compounds of the invention are non-toxic and do not induce photocytotoxicity. As they are selective for the G-quadruplex of c-MYC, they do not have side effects caused by inhibition or association with alternative conformations.

Tumors that are mediated by the expression of c-MYC are readily identified by assays known in the art. One illustrative assay relies on extraction and amplification of RNA using primers specific to the c-MYC transcript. A specific protocol for such an assay is set forth in Example 7.

The compounds of the invention are expanded porphyrins as described previously. They contain at least two selenium, sulfur and/or tellurium atoms in place of nitrogens in the pyrrole rings or pyrrole ring mimics. "Pyrrole ring mimics" are locations in the macrocycles formed in the expanded porphyrins where nitrogen is placed in a position where a pyrrole ring nitrogen would reside—i.e., between two carbon atoms, but the remaining two carbon atoms of the pyrrole are missing from the ring. The "pyrrole ring mimic" could be considered a "straight chain pyrrole" or a "minimized pyrrole."

It is important that the selenium, tellurium or sulfur atoms be spaced at an appropriate distance in the expanded porphyrins. They are spaced, typically, at a distance greater than that generated by four intervening σ bonds, and are in the range of 5–15 Å, preferably 6–10 Å, apart.

It is already known in the art that certain porphyrins and expanded porphyrins, some of the porphyrins having selenium substitutions, interact with G-quadruplexes in general, However, these are either of insufficient affinity, insufficient selectivity, or insufficient in their non-toxic and non-phototoxic properties.

Figure 1:
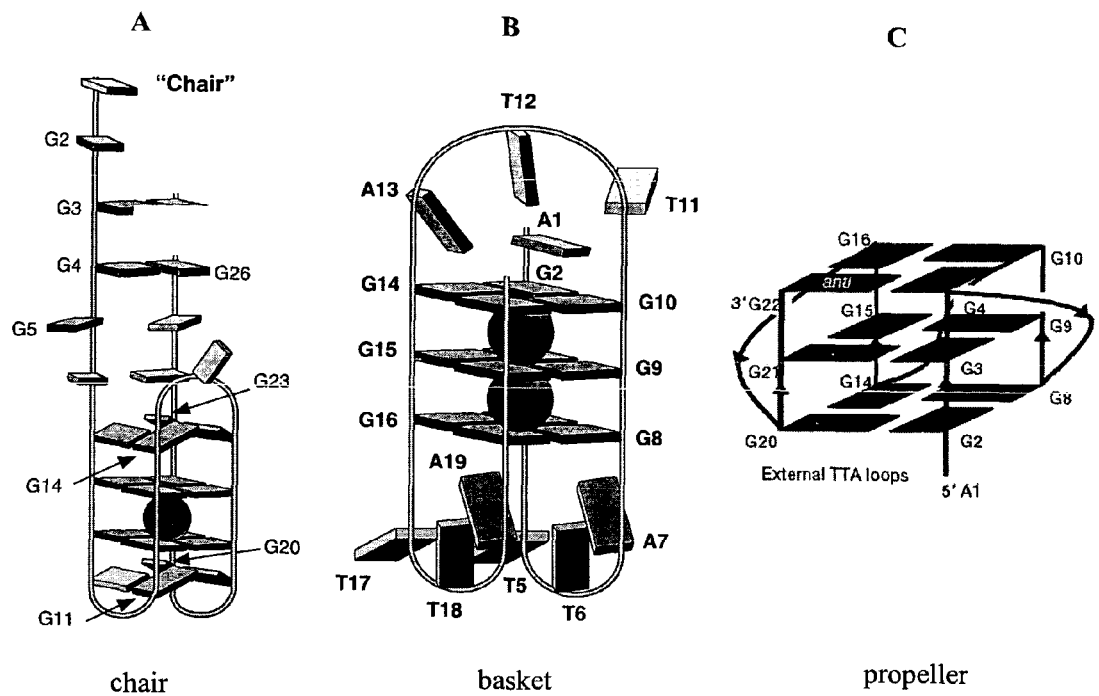
FIGS. 1A–C show the structural polymorphism in G-quadruplex structures.
Figure 2:
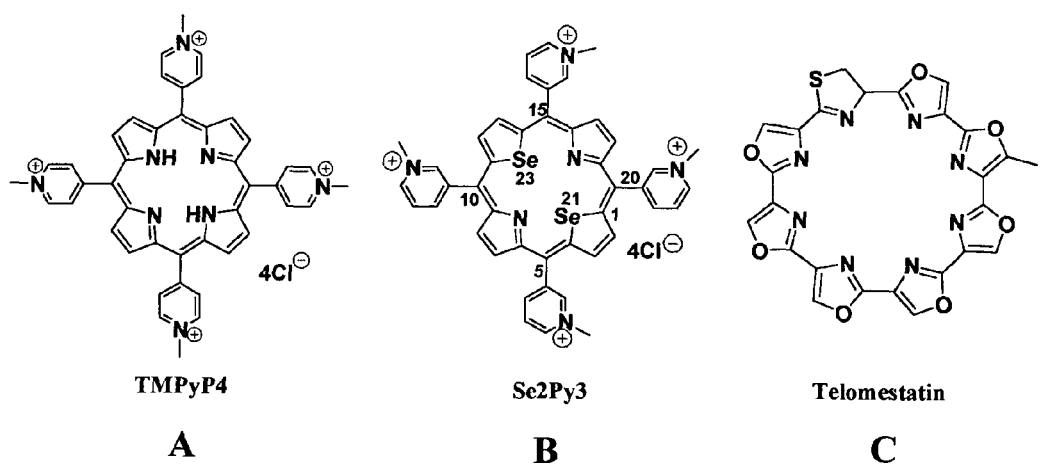
FIGS. 2A–2C show previously described G-quadruplex interactive compounds.
Figure 3A:
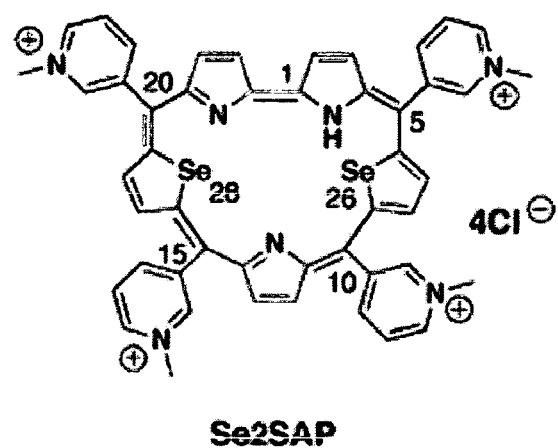
FIGS. 3A–3B show the structure of Se2SAP (FIG. 3A) and a superimposed model of this structure on the structure of telomestatin (FIG. 3B).
Figure 3B:
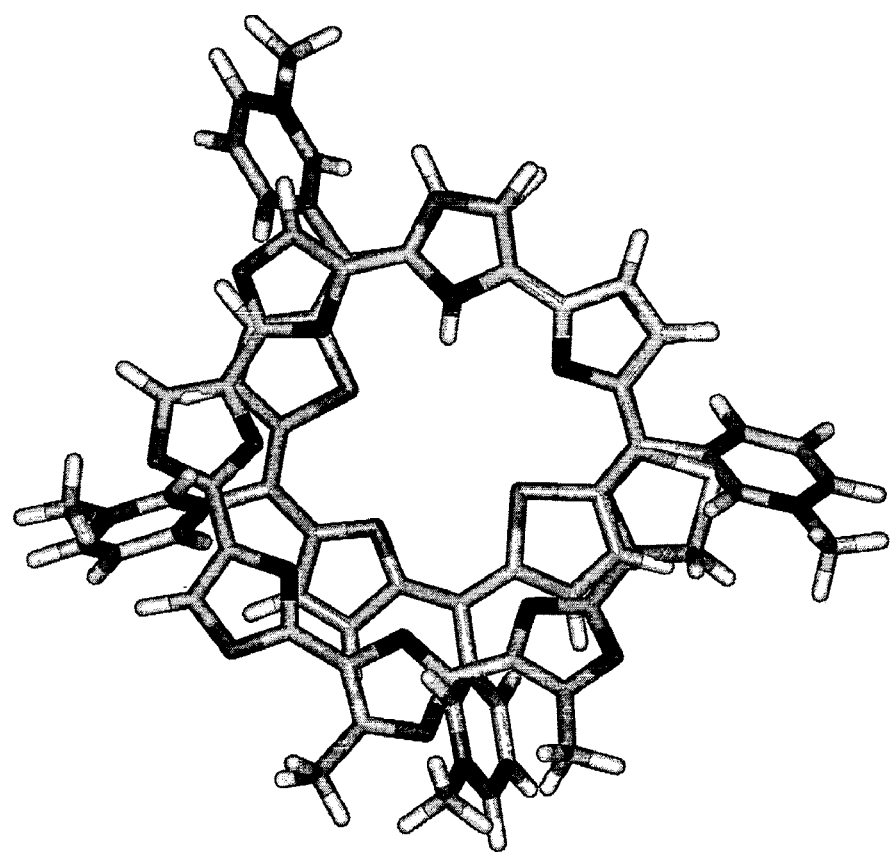

Porphyrins are per se known to produce photoinduced cytotoxicity, and selenium substitution for nitrogen in the core of porphyrin has been used to correct this. Thus, Se2Py3, (FIG. 2B) a diselenium substituted porphyrin has been used to study the interaction with both the chair and basket type G-quadruplex structures. Telomestatin, (FIG. 2C) a natural product, is known to bind strongly and stabilize both the intramolecular chair and basket type G-quadruplex structures. Based upon the improved binding of Se2Py3 to the chair type G-quadruplex structure and comparative molecular modeling with telomestatin (FIG. 3B), an expanded porphyrin Se2SAP (FIG. 3A) was designed and synthesized which was subsequently demonstrated to have dramatically improved selectivity for the G-quadruplex of c-MYC structure over both nucleic acid duplexes and the telomerase type G-quadruplex structure.

Using Se2SAP as a model, the structural motifs for ligands having selectivity towards c-MYC type G-quadruplex structure have been identified.

The advantages of the model Se2SAP over compounds in the art are shown below:

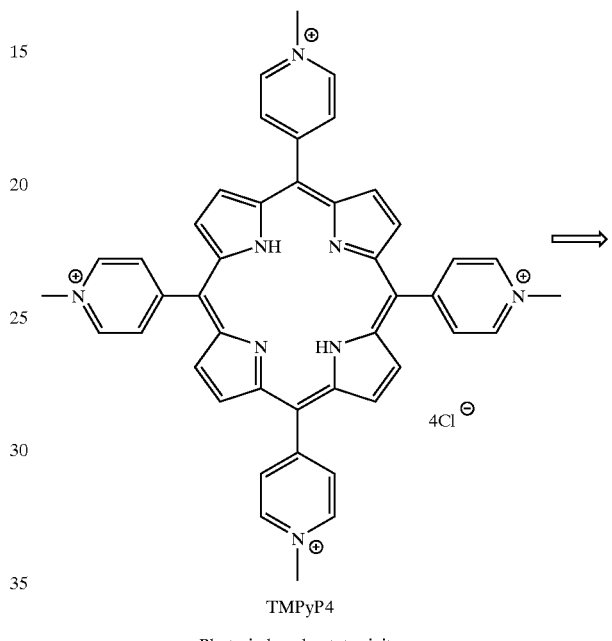

TMPyP4

Photo induced cytotoxicity
For c-myc type G-quadruplex
19 fold selectivity
Moderate binding Se2Py3

No photo induced cytotoxicity
For c-myc type G-quadruplex
30 fold selectivity
Strong binding -continued

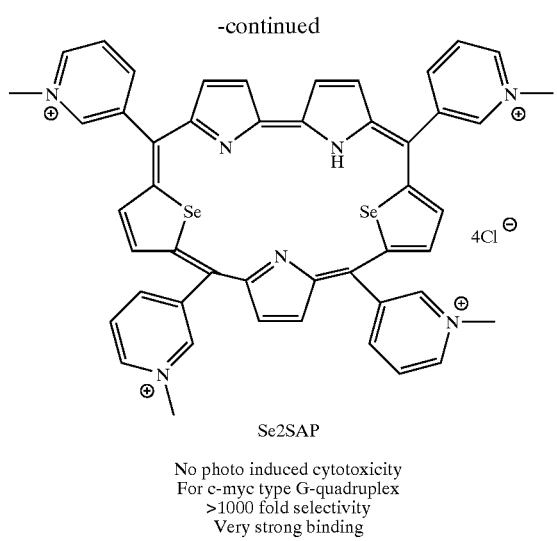

Se2SAP

No photo induced cytotoxicity
For c-myc type G-quadruplex
>1000 fold selectivity
Very strong binding To summarize, TMPyP4 shows a 19 fold, Se2Py3 a 30 fold and Se2SAP greater than 1,000 fold selectivity towards the c-MYC G-quadruplex. In contrast there is only 5 fold selectivity of the telomestatin towards c-MYC G-quadruplex structure. Introduction of selenium with proper positioning into the core of the porphyrin ring not only increases selectivity but also increases binding towards c-MYC G-quadruplex structure.

Even though, Se2Py3 and telomestatin show a strong stabilization of c-MYC G-quadruplex at low concentrations, they also exhibit duplex DNA binding at higher concentrations. This results in an increase in the c-MYC expression (up to 300%) with increase of concentration in Se2Py3 putatively due to the increasing preference of this molecule for duplex DNA with increased concentration. Se2SAP and TMPyP4, however, show little or no duplex binding activity. (It is known that there is an increase of 3-fold on c-MYC expression when mutations are made to the NHE III, such that the G-quadruplex cannot form.) Further, though Se2SAP shows a stabilization of c-MYC G-quadruplex greater than TMPyP4, its the inhibitory effect on c-MYC transcription is same as that of TMPyP4, suggesting that $Se_2SAP$ may be less susceptible to cellular uptake than TMPyP4.

Figure 4A:
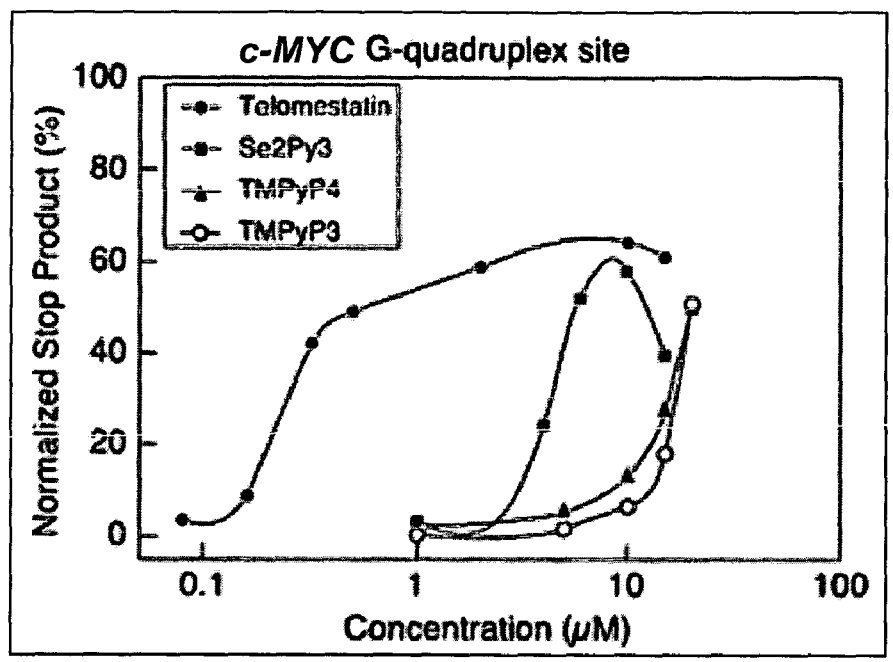
FIGS. 4A and 4B are graphs of percentage of stop product obtained at various concentration of prior art compounds.
Figure 4B:
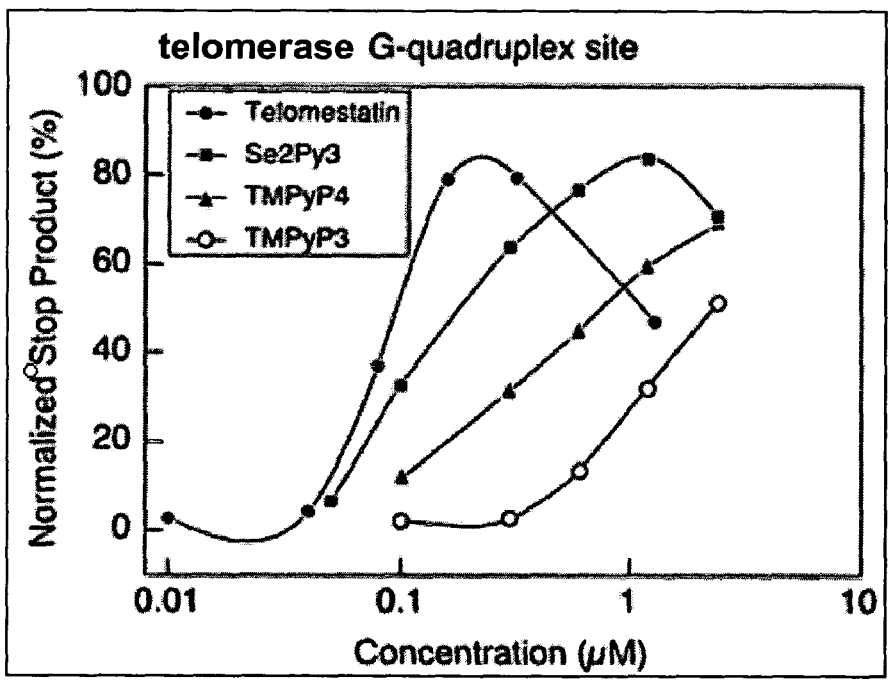

In contrast, a linear correlation is not seen with the human telomeric G-quadruplex structure (FIG. 4B).

Se2SAP is not photoactive and shows no cytotoxicity. This is due to the substitution of Se for NH, as is required in the compounds of the invention.

The Invention Compounds

In general, the compounds of the invention have an expanded porphyrin structure which is defined as comprising at least five pyrrole moieties or pyrrole moiety mimics. Pyrrole moiety mimics are defined as a nitrogen coupled to two carbons which are in turn coupled to the remainder of the porphyrin nucleus; thus, the "pyrrole mimic" is a pyrrole moiety which lacks the ring structure but provides the relevant linkage to the remainder of the porphyrin. The second feature of the compounds of the invention is that they contain at least two sulfur, selenium, and/or tellurian atoms spaced so as to interact with two carbonyl groups in the G-quadruplex. Thus, these two moieties are spaced at a distance of 5–15 Å, preferably 6–10 Å, from each other. The S, Se, and/or Te atoms occupy the positions that would otherwise have been occupied by NH in a pyrrole or pyrrole mimic in the expanded porphyrin. Typically, therefore, they replace NH moieties on non-adjacent pyrroles, i.e., pyrroles separated by one or more pyrroles or pyrrole mimics.

In the compounds of the invention, both of such two minimal replacements may be S, both Se, or both Te, or one may be S, the other Se, etc. Preferably, the replacements are by Se.

Additional substituents are also desired on the bridging positions of the porphyrin nucleus, whereby substituents which are, or may become, cationic are included. Thus, the substituents will include quaternary amines as well as primary, secondary or tertiary amines which may assume cationic status under physiological conditions.

Thus, the bridging atoms between the pyrrole moieties may be substituted by alkyl (1–6C), alkenyl (2–6C) or aryl wherein each of these substituents may contain or be modifiable to contain a cation. Typically, the cation is formed by virtue of the presence of at least one nitrogen atom. At least one such substituent must contain or be modifiable to contain a cation at physiological pH. Thus, the substituents represented by $R^1$ in formulas (1)–(20) may be in any bridging position, including aryl groups, not just in the exemplary positions shown.

"Alkyl" includes straight or branched chain or cyclic forms of saturated monovalent hydrocarbon; alkenyl is similarly defined except that at least one π bond is present. Aryl substituents are typically 5–6 membered rings optionally containing one or more heteroatom selected from O, S and N, and wherein the rings have the characteristics of an aromatic system. Such rings include phenyl, pyridyl, pyrimidinyl, and the like.

The expanded porphyrins may also be further substituted by non-interfering substituents; typically, the pyrrole nuclei may contain alkyl substituents and carbons contained in pyrrole nuclei may be replaced by O or S.

The synthesis of the various compounds included within the scope of the invention is achieved by standard chemical syntheses as is understood in the art; the following reaction schemes are illustrative. Synthesis may be conducted in solution or a solid phase synthesis may be employed.

Reaction Scheme 1 shows the solution phase synthesis of intermediate A wherein the Ar substituents shown in the methylene bridges may optionally be replaced by H, alkyl (1–6C), alkenyl (2–6C) and wherein each of these groups may comprise a cation or a group able to form a cation, typically an amino group. As shown, the synthesis begins with a simple pyrrole analog and ultimately results in intermediate A which can then be reacted with coupled pyrroles to obtain the expanded structures shown.

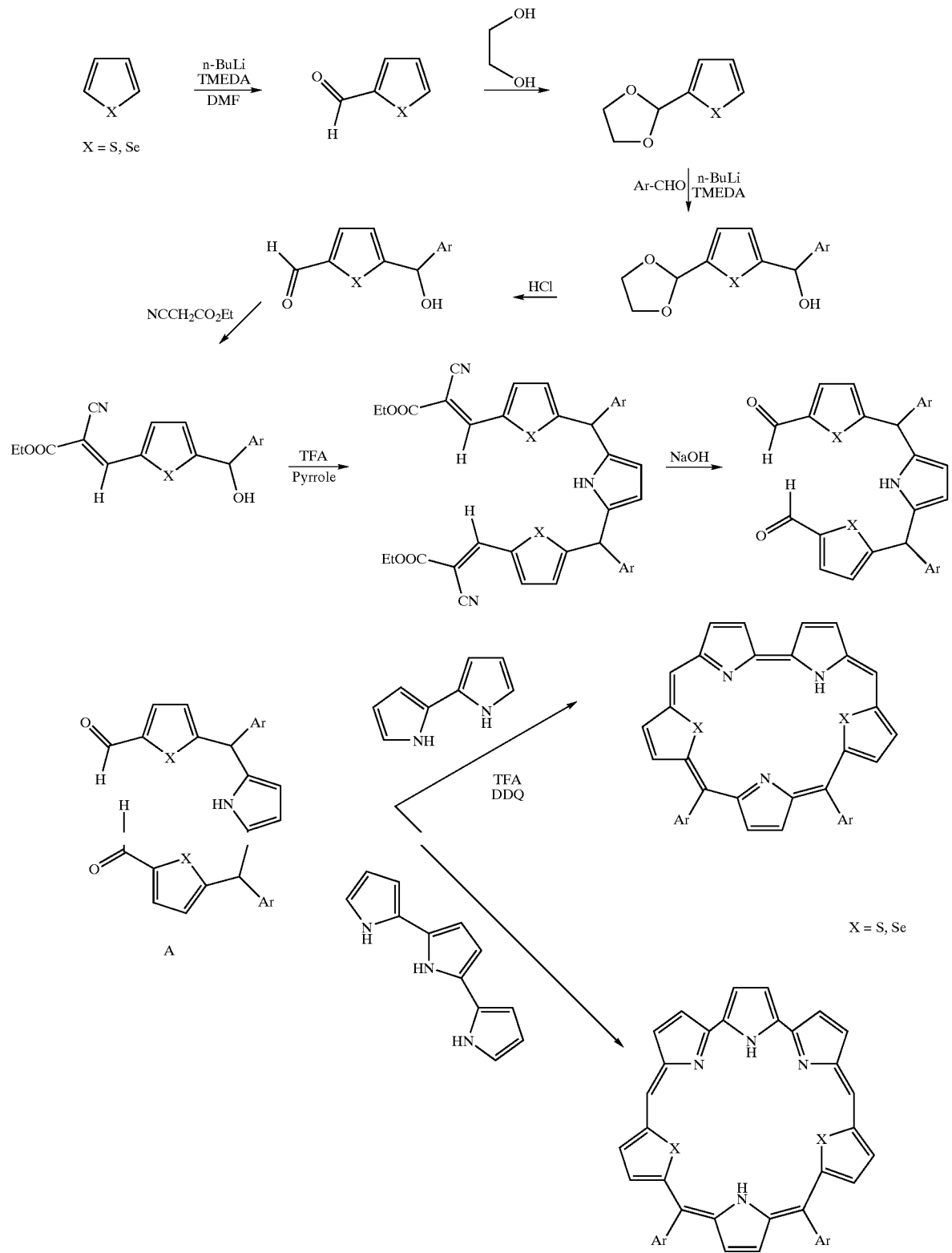
Reaction Scheme 1
Solution Phase Synthesis
X = S, Se

Alternatively, the same intermediate A may be obtained by solid phase synthesis and then condensed to form similar structures as shown in Reaction Scheme 2.
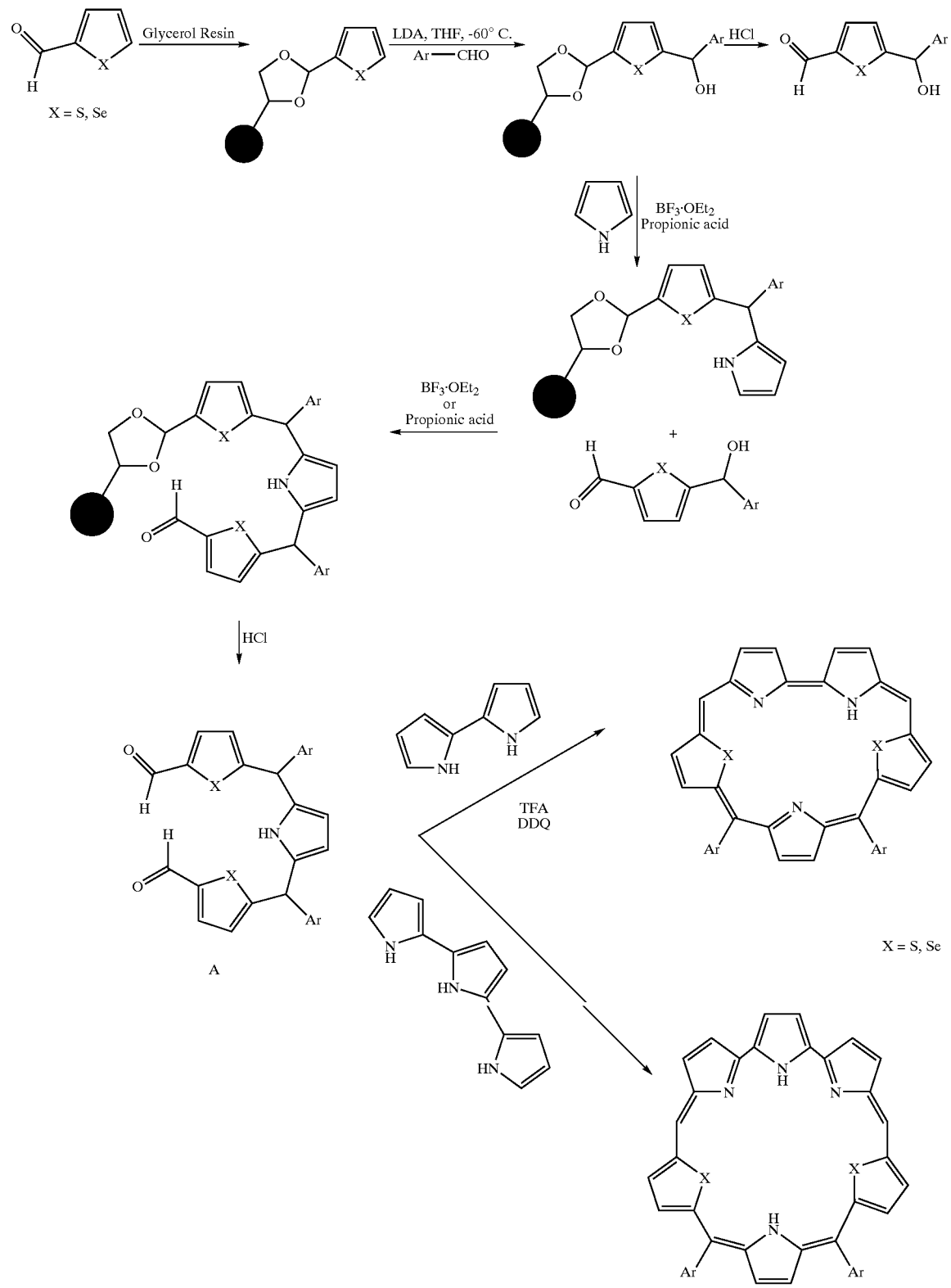
Reaction Scheme 2
Solid Phase Synthesis This intermediate can be used to obtain a variety of compounds of the invention as shown in Reaction Scheme 3.
Reaction Scheme 3
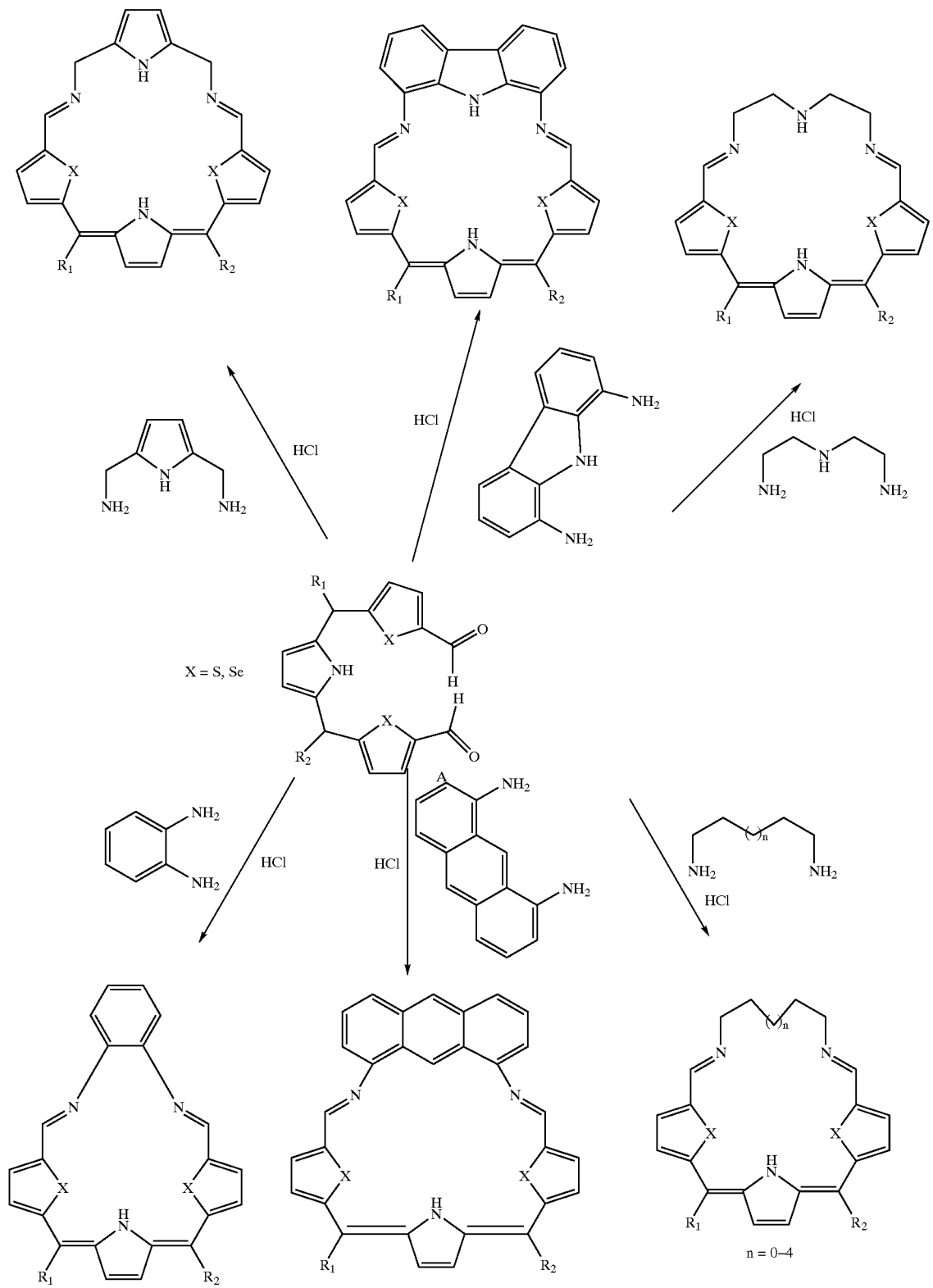

Alternative syntheses to obtain additional compounds of the invention are shown in Reaction Schemes 4 and 5.
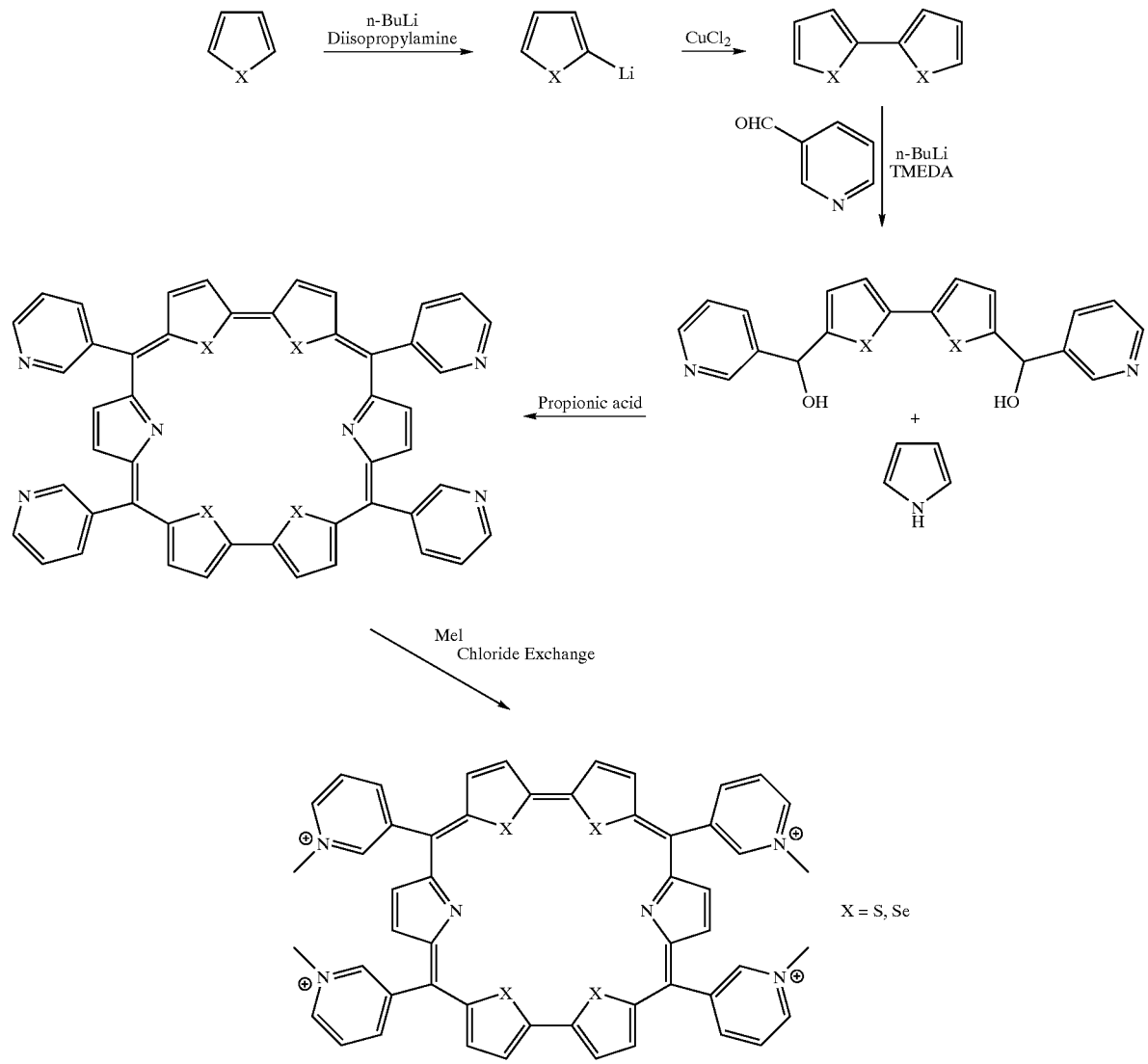
Reaction Scheme 4
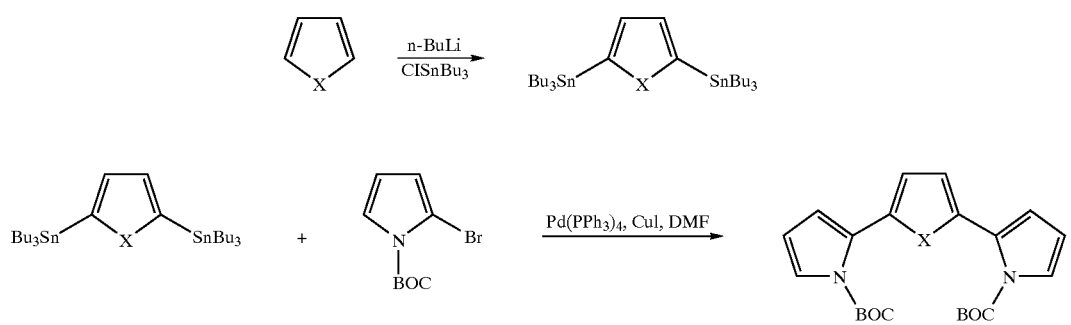
Reaction Scheme 5

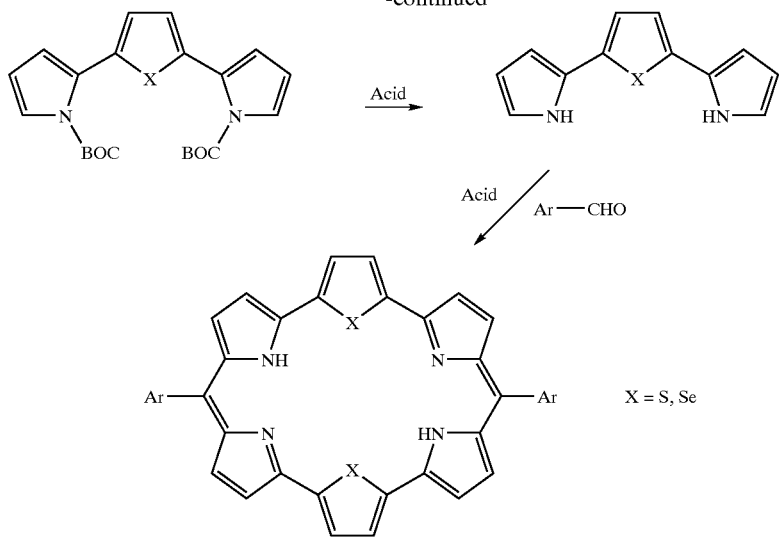

Again, the moiety represented by Ar may include a cation or cation-forming substituent.

Administration and Use

The compounds of the invention are useful in the treatment of malignancies that result from expression of the c-MYC gene. Such malignancies include tumors associated with breast, ovary, pancreas, bone, prostate, lung, kidney, liver, colon and lung, to name a representative number. The subjects comprising said tumors may be any vertebrate subject, including humans, domestic animals, birds, rodents, rabbits, and farm animals such as pigs, cows, horses and sheep.

Tumors that are characterized by expression of the c-MYC gene can be identified, if necessary, by determining elevated levels of expression as described in Example 7.

The dosage levels of the compounds of the invention are in the range of 0.1 µg/kg–10 mg/kg and are dependent on the route of administration. The compounds can be administered by any standard method, including oral, transmucosal, transdermal, injection, or suppository. Suitable formulations for such modes of administration may readily be found in *Remington's Pharmaceutical Sciences,* latest edition, Mack Publishing Co., Easton, Pa., incorporated herein by reference. The exact dosage level, the desired route, and the mode of administration will depend on the nature of the subject, the particular compound of the invention selected, the severity of the condition of the subject, the general health of the subject, and the judgment of the attending practitioner.

Further, it is recognized that the compounds of the invention may be modified to improve their delivery characteristics in vivo, to assist in their purification, to assist in their detection, and the like. Accordingly, the invention compounds may be provided as "conjugates" wherein the structure shown is coupled to one or more additional moieties. For example, the compounds described and claimed may be coupled to a polyethylene glycol moiety to enhance half-life, to an antibody to target-specific sites in vivo, to an antigen to assist in purification on an antibody column, to a label in order to permit detection of the compound, and numerous other embodiments which will be evident to the skilled artisan. Thus, the claims herein are directed not only to the compounds per se, but also to "conjugates" of the compounds wherein the compound itself is coupled to an auxiliary moiety. The nature of the auxiliary moiety will be reflected in the purpose for which it is attached. The selection of an appropriate moiety for any specific application would be well within the ordinary skill of the practitioner.

The following examples are intended to illustrate but not to limit the invention.

EXAMPLE 1

Preparation of 5,10,15,20-tetra(3-pyridyl)-21,23-diselenaporphyrin and 5,10,15,20-tetra(3-pyridyl)-26,28-diselenasapphyrin This example describes the preparation of the prior art compound Se2Py3 and the compound of the invention Se2SAP. An overview of this synthesis is as follows:

The synthesis employed the following scheme:

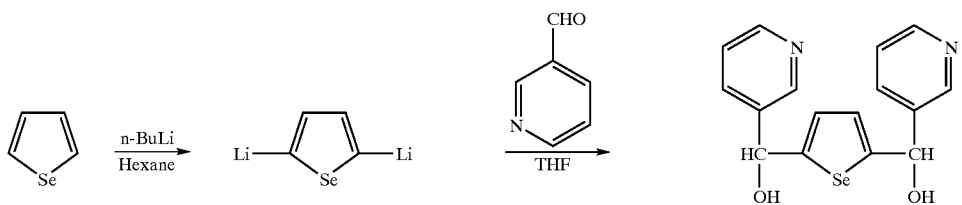

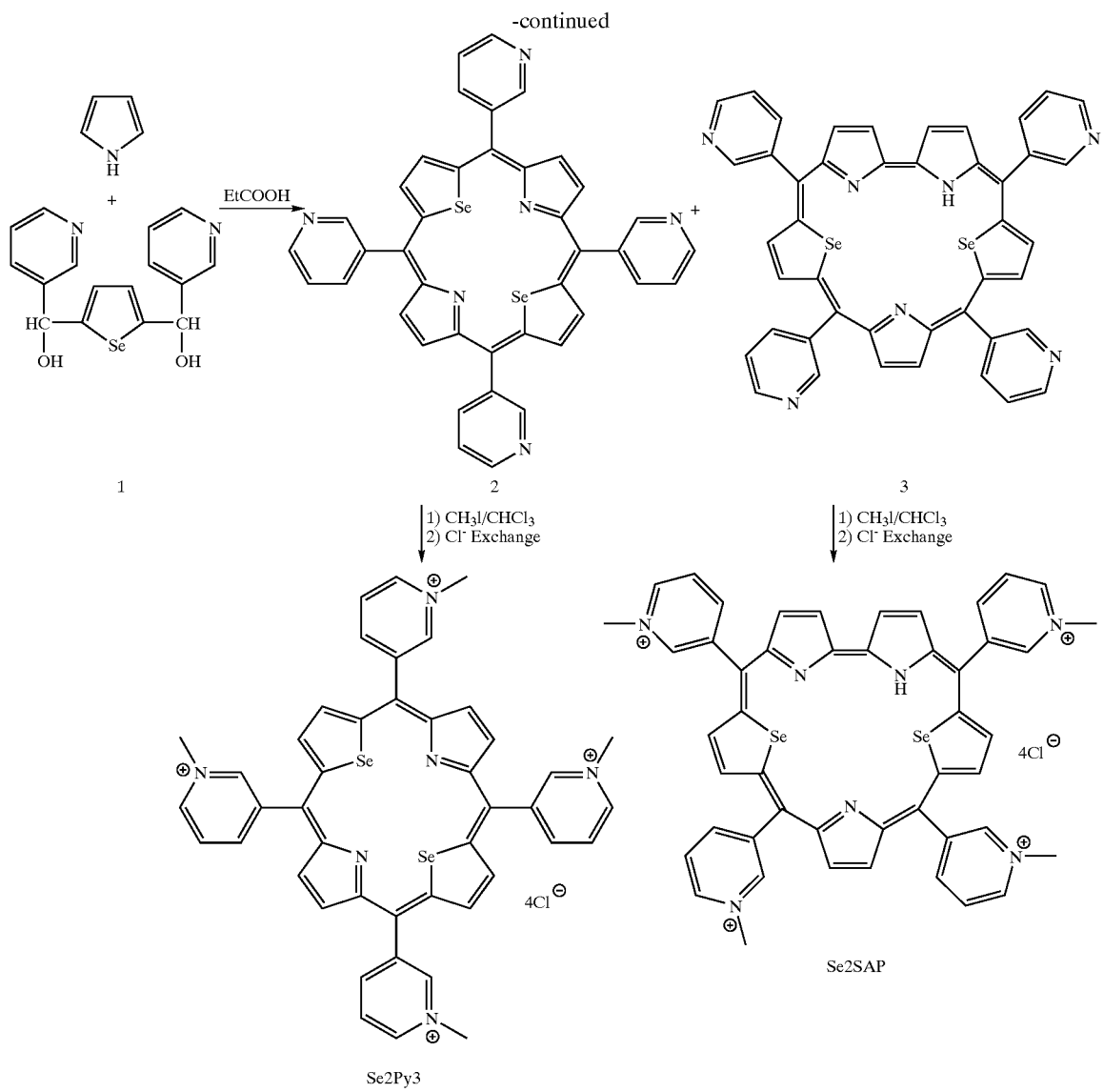

In general, selenophene was lithiated in the 2 and 5 positions and converted to the diols by reacting with pyridyl aldehydes. The yields of the diol were dependent on the aldehyde used (40% for 3-pyridine substituted diol and 25% for 4-pyridine substituted diol). The diol was then condensed with pyrrole in presence of acid to obtain the porphyrin. The porphyrin obtained was further methylated in the pyridine nitrogen using methyl iodide. The chloride ion was exchanged for iodide ion using ion exchange resin. The presence of pyridyl rings restricted us to use only propionic acid. The use of other acids such as TFA, BF3.OEt2 and acetic acid did not yield any porphyrins.

Condensation of 2,5-bis[(4-pyridyl)hydroxymethyl] selenophene with pyrrole in propionic acid did not yield the expected diselena porphyrin, 5,10,15,20-tetra-(N-methyl-4-pyridyl)-21-23 diselena porphyrin (Se2Py4) but 5,10,15,20-[tetra-(N-methyl-3-pyridyl)]-21-23-diselenaporphyrin (Se2Py3) was synthesized. 5,10,15,20-[tetra-3-pyridyl]-21-23-diselena porphyrin (2) was synthesized in 5% yield by the condensation of 2,5-bis[(3-pyridyl)hydroxymethyl] selenophene (1) with pyrrole in propionic acid. This was further methylated to produce Se2Py3 (Scheme 1).

Demethyl Se2SAP was obtained as a minor product (1–2% yield) in the synthesis of unmethylated Se2Py3. The difficult task resides in purification of this minor product from the more abundant linear chain compounds and demethyl Se2Py3. Repeated purification with preparative TLC was required for purification since the $R_f$ values for both demethyl Se2Py3 and Se2SAP are very close. Subsequently purified demethyl Se2SAP was subjected to further methylation and ion exchange with chloride ion to obtain Se2SAP. $^1$HNMR showed two fold symmetry at room temperature due to the NH tautomerism in the bipyrrole ring. Absorption spectra in water as a solvent showed the aggregative nature of the molecule. The Soret and Q-bands are shifted to red compared to Se2Py3 and is due to the extended conjugation in the 22π ring of Se2SAP.

In this example, $^1$H NMR were run on a Varian Unity 300-MHz NMR Spectrophotometer. The chemical shifts are relative to the trace proton signals of the deuterated solvent.

Coupling constants, J, are reported in Hz and refer to apparent peak multiplicity rather than coupling constants. Flash column chromatography was performed on silica gel 60, 230–400 mesh, purchased from Spectrum. Basic alumina was used for purifying porphyrins in column chromatography. All starting materials were obtained from commercial sources unless otherwise specified.

Preparation of 2,5-bis(3-pyridylhydroxymethyl)selenophene

To a three necked, round bottomed flask flushed with argon was added 150 mL of anhydrous hexane, 14.4 mL (0.09 mol) of TMEDA and 60 mL (1.6M in hexane) (0.09 mol) of n-butyllithium, 3.5 mL (0.04 mol) of selenophene was then added at room temperature, the mixture was refluxed for 1 h. After cooling to room temperature, the suspension formed was slowly transferred dropwise via needle to a degassed solution of 9.04 mL(0.09 mol) 3-pyridinecarboxaldehyde in 250 mL of anhydrous THF. After the addition was completed, the mixture was stirred for overnight. Ice cold $NH_4Cl$ was added to quench the reaction. The phases were separated and the water layer was extracted with 1:6 methanol-chloroform mixture. The organic layers were combined, washed with water and dried over $Na_2SO_4$. After removal of solvent, the residue was purified by chromatography on silica gel using chloroform-methanol (8:1) as eluent to give 4.6 g (35%) of the product. $^1$HNMR (DMSO-$d_6$) δ 8.59 (s, 2H), 8.45 (dd, J=4.7 Hz, 2H), 7.77 (dd, J=4.7 Hz, 2H), 7.32–7.37 (dd, J=4.7 Hz, 2H), 6.87 (d, 2H), 6.45 (br s, 2H), 5.91 (s, 2H); HRMS (FAB) calcd. for $C_{16}H_{15}O_2N_2Se$: 347.0299; found: 347.0297.

Preparation of 2,5-bis(4-pyridylhydroxymethyl)selenophene 2,5-bis(4-pyridylhydroxymethyl)selenophene was prepared by a reaction of 9.04 mL (0.09 mol) 4-pyrdinecarboxaldehyde with 3.5 mL (0.04 mol) selenophene by a procedure similar to that described above. The 2,5-bis(4-pyridylhydroxymethyl)selenophene was obtained in 20% yield. $^1$H NMR (DMSO-$d_6$) δ 8.48 (d, J=3.4 Hz, 4H), 7.36 (d, J=3.4 Hz, 2H), 7 6.87 (s, 2H), 6.93 (s, 2H), 6.44 (brs, 2H), 5.82 (s, 2H); HRMS (FAB) (M$^+$) calcd. for $C_{16}H_{15}O_2N_2Se$: 347.0299; found, 347.0301.

Preparation of 5,10,15,20-tetra(3-pyridyl)-21,23-diselenaporphyrin and 5,10,15,20-tetra(3-pyridyl)-26,28-diselenasapphyrin A mixture of 1.2 g (3.49 mmol) of 2,5-bis(3-pyridylhydroxymethyl)selenophene and 0.247 ml (3.49 mmol) of pyrrole was dissolved in 200 mL of propionic acid. The mixture was refluxed for 48 h. After cooling to room temperature, the solvent was evaporated to dryness under high vacuum. The residue was purified by chromatography on basic alumina using 5% methanol and dichloromethane to give the mixture of diselena porphyrin and diselenasapphyrin. This was further purified several times by column and PTLC to separate the mixture. The yields 3% and 1% are for the diselenaporphyrin and diselenasapphyrin respectively.

For diselenaporphyrin $^1$H NMR (CDCl$_3$) δ 9.95 (s, 4H), 9.56 (s, 4H), 9.13 (d, J=4.7 Hz, 4H), 8.88 (s, 4H), 8.64 (d, J=7.6 Hz, 2H), 7.86–7.90 (m, 4H); UV-vis (CH$_2$Cl$_2$) $\lambda_{max}$ (nm) ($\epsilon \times 10^{-4}$) 443 (2.89), 524 (0.49), 626 (0.10), 688 (0.08), 723 (0.05); HRMS (FAB) (M$^+$) calcd. for $C_{40}H_{25}N_6Se_2$: 749.0480; found, 749.0491. For diselena sapphyrin $^1$H NMR (CDCl$_3$) δ 10.50 (d, J=5.1 Hz, 2H), 10.38 (d, J=5.1 Hz, 2H), 10.12 (d, J=3.7 Hz, 2H), 9.77 (s, 2H), 9.67 (s, 2H), 9.38 (d, J=4.5 Hz, 2H), 9.27 (d, 2H), 9.22 (d, 2H), 9.00 (s, 2H), 8.82 (d, 2H), 8.73 (d, J=7.4 Hz, 2H), 7.98–8.01 (m, 2H), 7.90–7.94 (m, 2H); UV-vis (CH$_2$Cl$_2$) $\lambda_{max}$ (nm) ($\epsilon \times 10^{-4}$) 476 (20.35), 593 (1.59), 632 (0.87), 733 (0.40), 821 (1.41); HRMS (FAB) (M$^+$) calcd. for $C_{44}H_{28}N_7Se_2$: 814.0747; found, 814.0745.

Preparation of 5,10,15,20-tetra(N-methyl-3-pyridyl)-21,23-diselenaporphyrin chloride 15.0 mg (0.02 mol) of diselenaporphyrin was dissolved in 5.0 mL of chloroform and diluted with 3.0 mL of nitromethane. 3.0 mL of iodomethane was added and the mixture was heated to reflux under argon for 24 h. After removal of solvent to dryness, 5.0 mL of water was added to the residue and treated with 2.0 g of Dowex 1×2-200 anion exchange resin in the chloride form, shaking slowly for 2 h. The resin was filtered off, washed with water, and the filtrate lyophilized to give the chloride salt of Se2Py3 (70%). $^1$H NMR (DMSO-$d_6$) δ 10.25 (s, 4H), 10.06 (s, 4H), 9.54 (d, J=6.0 Hz, 4H), 9.25 (d, J=7.6 Hz, 4H), 9.08 (s, 4H), 8.61–8.66 (m, 4H), 4.66 (s, 12 H); UV-Vis (DMSO) $\lambda_{max}$ (nm) ($\epsilon \times 10^{-4}$) 443 (5.97), 526 (1.23), 624 (0.31), 685 (0.19), 725 (0.17); HRMS (ESI) [(M-2H)/2] calcd. for $C_{44}H_{34}N_6Se_2/2$: 402.0598; found, 402.0601.

Preparation of 5,10,15,20-tetra(N-methyl-3-pyridyl)-26,28-diselena sapphyrin chloride (Se2SAP)

The above procedure was followed using 15 mg (0.018 mmol) diselena sapphyrin and 2.8 mL (20 mmol) iodomethane. Se2SAP was obtained in 70% yield. $^1$H NMR (DMSO-$d_6$) δ 10.79 (d, J=5.6 Hz, 2H), 10.63 (d, J=5.7 Hz, 2H), 10.62 (d, 2H), 10.28 (s, 2H), 10.19 (s, 2H), 9.68 (d, 2H), 9.67 (d, 2H), 9.66 (d, 2H), 9.57 (d, 2H), 9.43 (d, 2H), 9.18 (s, 2H), 8.72–8.76 (m, 2H), 8.65–8.67 (m, 2H), 4.76 (s, 6H) 4.70 (s, 6H); UV-Vis (DMSO/TFA) $\lambda_{max}$ (nm) ($\epsilon \times 10^{-4}$) 484 (43.10), 599 (3.52), 634 (1.87), 729 (1.14), 830 (2.47); HRMS (ESI) [(M-2H)/2] calcd. for $C_{48}H_{37}N_7Se_2/2$: 435.5726; found, 435.5721.

EXAMPLE 2

G-Quadruplex Polymerase Stop Assay

In this example, compound solutions were prepared as 1 mM stock solutions in dimethyl sulfoxide and stored at −20° C. These stock solutions were diluted to working concentrations in distilled water immediately before use. Electrophoretic reagents (acrylamide/bisacrylamide solution and ammonium persulfate) were purchased from BioRad, and N,N,N',N'-tetramethylethylenediamine (TEMED) was purchased from Fisher. T4 polynucleotide kinase, Taq DNA polymerase, and human topoisomerase II were purchased from New England Biolabs, Promega, and TopoGen, respectively. [γ-$^{32}$P] ATP was purchased from NEN Dupont.

Oligonucleotides were synthesized on an Expedite 8909 nucleic acid synthesis system (PerSeptive Biosystems, Framingham, Mass.) using the phosphoramidite method. The oligonucleotides were eluted out of the column by using aqueous ammonia and deprotected by heating at 55° C. overnight, followed by 15% denaturing polyacrylamide gel purification. Prior to the experiment, all oligonucleotides were treated in 10 mM NaOH for 30 min at 37° C. followed by neutralization with 10 mM HCl and ethanol precipitation in order to disrupt the self-associated structures. The 5'-end-labeled single-strand oligonucleotide was obtained by incubating the oligomer with T4 polynucleotide kinase and [$\gamma$-$^{32}$P]ATP for 1 h at 37° C. Labeled DNA was purified with a Bio-Spin 6 chromatography column (BioRad) after inactivating the kinase by heating for 8 min at 70° C.

For the stop assay, the DNA primers were: d[TAATAC-GACTCACTATAGCAATT GCGTG]

the human telomeric template sequence, d[TCCAACTAT-GTATAC(TTAGGG)$_4$TTAGC GGCACGCAATTGC-TATAGTGAGTCGTATTA] and the PU27 c-MYC template sequence d[TCCAACTATG-TATAC(GGAAGGGGTGGGA GGGGTGG-GAGGGGT)TTAGCGGCACGCAATTGCTATAGT-GAGTCGTATTA].

These were synthesized and purified as described above. Labeled primer (100 nM) and template DNA (100 nM) were annealed in an annealing buffer (50 mM Tris-HCl, pH 7.5, 10 mM NaCl) by heating to 95° C. and then slowly cooled to room temperature. DNA formed by annealing the primer to the template sequence was purified using gel electrophoresis in the 12% native polyacrylamide gel. The purified DNA was then diluted to the concentration of 2 nM and mixed with the reaction buffer (10 mM MgCl$_2$, 0.5 mM DTT, 0.1 mM EDTA, and 1.5 $\mu$g/$\mu$L BSA) and 0.1 mM dNTP. KCl and NaCl (10 mM each) were added to the reaction. Taq DNA polymerase was added, and the mixture was incubated at 55° C. for 20 min. The polymerase extension was stopped by adding 2× stop buffer (10 mM EDTA, 10 mM NaOH, 0.1% xylene cyanole, 0.1% bromophenol blue in formamide solution) and loaded onto a 16% denaturing gel.

DNA extension by Taq polymerase is paused at the G-quadruplex forming site. The extent of stoppage that occurs is used as a measure of the stabilization of the G-quadruplex structures by various ligands.

The relative binding affinity of porphyrins to the intramolecular c-MYC G-quadruplex structure was determined by incubating increasing concentrations of each porphyrin or telomestatin with a DNA template containing PU27-c-MYC sequence [GGAAGGG GTGGGAGGGGTGGGAGGGGT] at 55° C. in presence of Taq polymerase as described above. Since there was a considerable amount of pausing (attributable to the presence of K$^+$ ion in the buffer that facilitates G-quadruplex formation) in the absence of drug elevated temperatures (55° C.) were used to partially destabilize the arresting G-quadruplex structure and thereby permit a larger window for drug stabilization of the G-quadruplex structure. For the intramolecular telomeric type G-quadruplex structure, a DNA template containing four repeats of the human telomeric sequence TTAGGG was used. In this case there was only very little Taq polymerase pausing in the absence of drug, so 37° C. was used as the incubation temperature. The G-quadruplex binding ability of Se2Py3 was compared with TMPyP4, TMPyP3 and the natural product telomestatin.

FIGS. 4A and 4B show the concentration dependent inhibition of polymerase DNA synthesis by ligand stabilization of the G-quadruplex structure formed on the DNA templates containing PU27 c-MYC and human telomeric sequences respectively. In each case there is a significant greater pausing at the G-quadruplex forming site in presence of increasing concentrations of compounds. For the Pu27-c-MYC sequence there is pausing at the primer position in the absence of drug and this is due to presence of free primer even after purification. Pausing at the G-quadruplex forming site is quantified as the normalized percentage of stop product with respect to the total intensity per lane. Pausing of polymerase processing at the primer position in presence of higher concentration of compounds is most likely due to ligand binding with single or double stranded DNA (data not shown). This is quantified as the normalized percentage of duplex product with respect to the total intensity per lane. ED$_{50}$ values calculated from the graphs are tabulated in Table 1.

TABLE 1

| Ligand | c-MYC (ED$_{50}$ $\mu$M) | Human Telomeric (ED$_{50}$ $\mu$M) | Duplex DNA (ED$_{30}$ $\mu$M) |
| --- | --- | --- | --- |
| Telomestatin | 0.11 | 0.59 | 11.11 (×100) |
| Se2Py3 | 0.17 | 5.82 | 9.40 (×55) |
| TMPyP4 | 0.99 | 18.90 | >50 (>50) |
| TMPyP3 | 2.34 | 19.50 | >50 (>50) |

The ED$_{50}$ values of Se2Py3 for both c-MYC and human telomeric sequence are intermediate ED$_{50}$ values of telomestatin and TMPyP4. This suggests that introduction of selenium in the porphyrin core increases the G-quadruplex binding to a considerable extent (4~5 fold) but its binding ability is still lower than the larger ring structure telomestatin. ED$_{50}$ values for TMPyP4 show that there is ~19 fold preference for the c-MYC G-quadruplex over the human telomeric G-quadruplex sequence. Thus, TMPyP4 already has a reasonable selectivity for the c-MYC G-quadruplex structure, and there is less duplex or single strand interaction than with telomestatin. In contrast, TMPyP3 showed only 8 fold preference for the c-MYC G-quadruplex over the human telomeric G-quadruplex sequence. In case of Se2Py3, there is ~34 fold preference for the c-MYC G-quadruplex sequence compared to the human telomeric G-quadruplex sequence. Therefore, introduction of selenium not only increases the binding of porphyrins with the G-quadruplex but also increases the selectivity for c-MYC G-quadruplex over the telomeric G-quadruplex structure. In contrast, telomestatin showed only ~5 fold preference for the c-MYC sequence over the human telomeric sequence. Thus, even though telomestatin has a strong binding with the G-quadruplex structures, it does not have appreciable selectivity between c-MYC and human telomeric G-quadruplex structures hastily. Telomestatin and Se2Py3 showed considerable duplex or single strand binding.

The conclusions from the above results are (i) introduction of selenium in the core of the porphyrin increases the binding with the G-quadruplex structure and enhances the selectivity towards c-MYC type G-quadruplex, (ii) telomestatin, a larger ring structure binds much strongly with both G-quadruplex structures.

EXAMPLE 3

Se2SAP selectively interacts with the c-MYC G-quadruplex structure

Figure 5A:
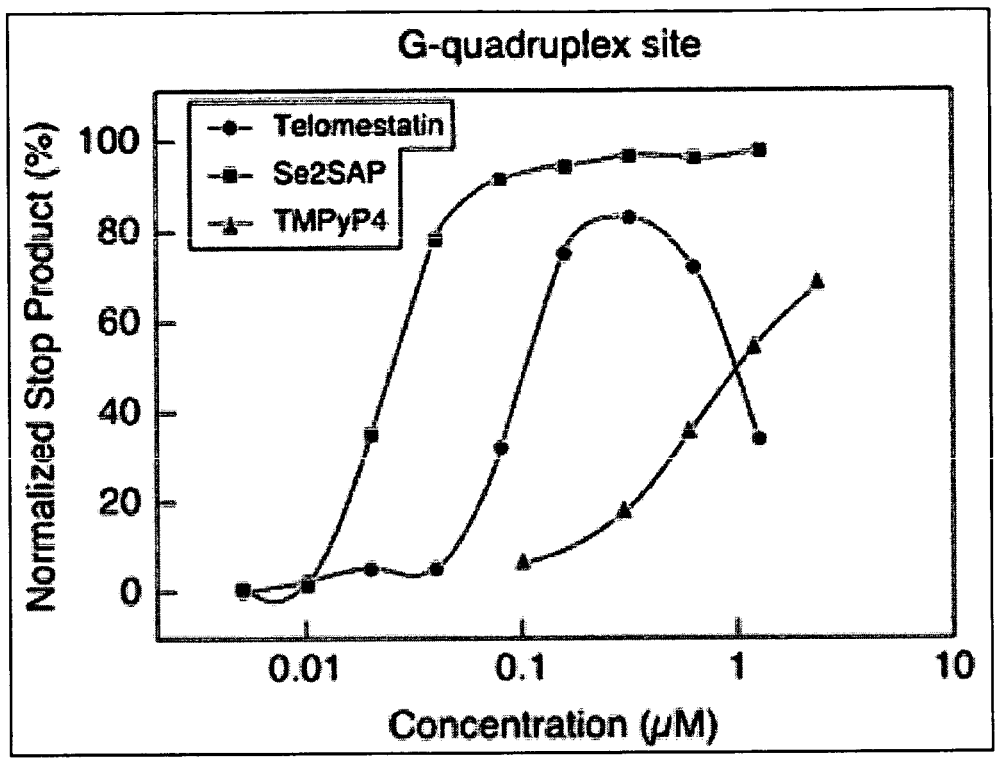
FIGS. 5A and 5B are graphs of the percentage of stop product obtained at various concentrations of Se2SAP, telomestatin, and TMPyP4.
Figure 5B:
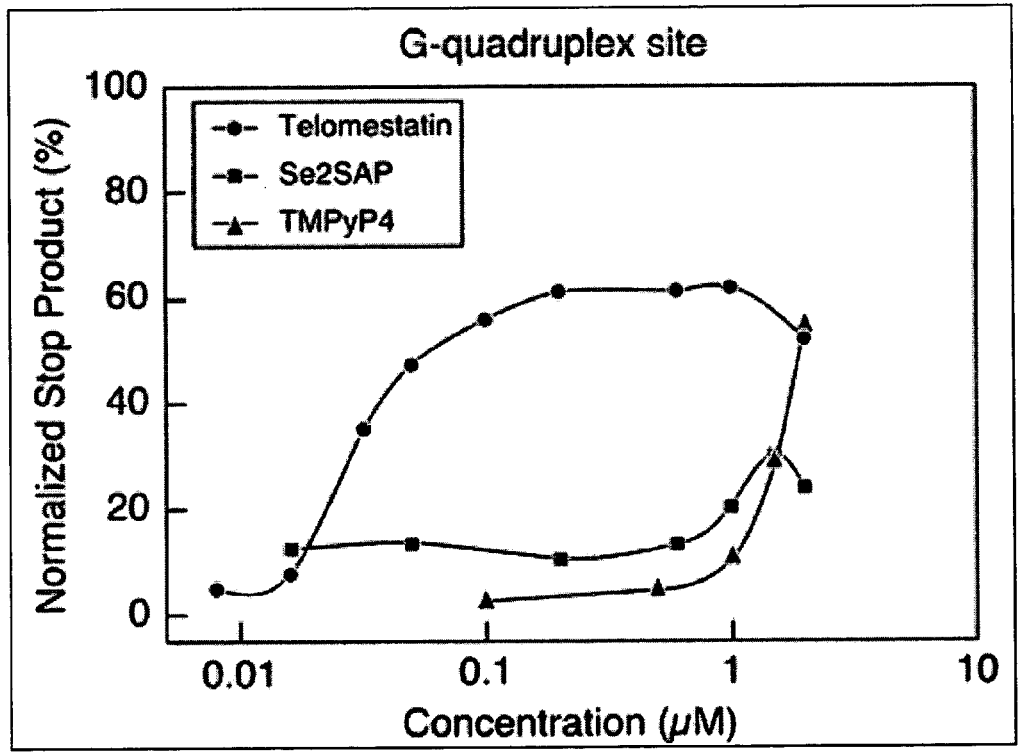

In order to determine the potential selectivity of Se2SAP for the c-MYC G-quadruplex, a polymerase stop assay was conducted with Se2SAP on the templates containing either the c-MYC or the human telomeric sequence as described in Example 2. The Se2SAP concentration dependent inhibition of polymerase DNA synthesis by the G-quadruplex structure formed on the DNA templates containing PU27 c-MYC and human telomeric sequences are represented in FIGS. 5A and 5B respectively. The Se2SAP showed a complete arrest of the polymerase synthesis at the concentration of 0.04 µM at the G-quadruplex forming site in the template containing c-MYC sequence (FIG. 5A). Conversely, there was little pausing in the polymerase synthesis by Se2SAP even at 20 µM in the G-quadruplex forming site using the template containing human telomeric sequence (FIG. 5B). Telomestatin showed a considerable pausing in the G-quadruplex forming site in both the sequences. The $ED_{50}$ values obtained from the graphs showed the most stabilization for Se2SAP ($ED_{50}$=0.025 µM) in comparison to telomestatin ($ED_{50}$=0.106 µM) and TMPyP4 ($ED_{50}$=0.99 µM) with the c-MYC chair type G-quadruplex. While there is a considerable duplex interaction for the telomestatin, the absence of duplex binding for Se2SAP in the c-MYC sequence shows selective recognition of G-quadruplex structure by this molecule. $ED_{50}$ value for the binding of telomestatin with the human telomeric G-quadruplex structure is 0.586 µM. Since, there is only very little interaction of Se2SAP with the human telomeric G-quadruplex structure, $ED_{50}$ values can't be calculated from the graph. These results clearly show the selectivity for and strong stabilization of the c-MYC G-quadruplex structure by Se2SAP.

EXAMPLE 4

Photomediated Strand Cleavage Reaction

Figure 6:
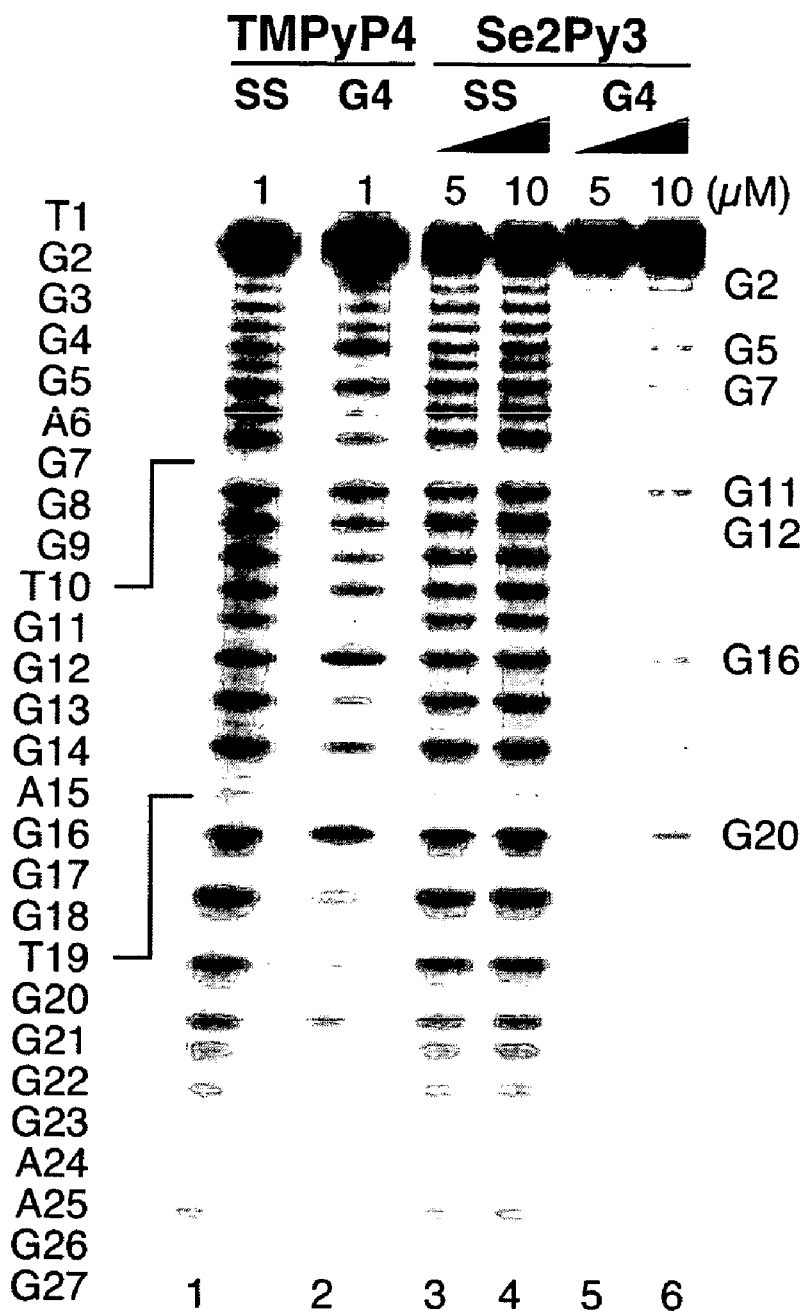
FIG. 6 shows a comparison of photo-induced cleavage of c-MYC G-quadruplex structure by TMPyP4 and Se2Py3 on a gel of the cleavage products.

Se2Py3 does not exhibit any fluorescence. The non-photo activity of Se2Py3 on the DNA was further confirmed using the photo mediated strand cleavage reaction on c-MYC G-quadruplex structure. Generally, photoactive porphyrins catalyze the oxidation of DNA upon exposure to light, which results in DNA strand breakage in proximity to the binding site of the porphyrins. The specific cleavage pattern of the G-quadruplex structures can be used to identify both the binding modes and sites of binding of porphyrins. This is shown in FIG. 6. Both TMPyP4 and Se2Py3 showed a similar cleavage pattern (lanes 2,5 and 6), which suggests that both the molecules have similar mode of binding in c-MYC G-quadruplex structure. TMPyP4 showed a considerable cleavage pattern at 1 µM (lane 2) whereas Se2Py3 show very little cleavage even at 10 µM (lane 6) and confirms the non-photo activity of Se2Py3.

In more detail, labeled template Pu27-c-MYC (10 nM) was heated to 95° C. and slowly cooled to room temperature in a buffer (50 mM Tris-HCl, pH 7.5, 5 mM NaCl, 5 mM KCl, 10 mM $MgCl_2$, 0.5 mM DTT, 0.1 mM EDTA, and 1.5 µg/µL BSA). A 1 mM final concentration of FQA was added and transferred to a 24-well Titertek microtiter plate (ICN). This plate was placed on top of a Pyrex glass shield and irradiated for 2 h with an 85-W xenon lamp placed under the Pyrex glass. Pyrex glass was used to filter the UV light under 300 nm, thereby eliminating DNA damage caused directly by UV irradiation. During the irradiation, the Titertek plate was rotated three times to eliminate light heterogeneity. Reactions were terminated by the addition of 10 µg of calf thymus DNA, followed by phenol-chloroform extraction and ethanol precipitation. The resulting samples were subjected to treatment with 0.1 M piperidine. The samples were then loaded onto a 12% sequencing gel.

The dried gels were exposed on a phosphor screen. Imaging and quantification were performed using a PhosphorImager (Storm 820) and ImageQuant 5.1 software from Molecular Dynamics.

Figure 7:
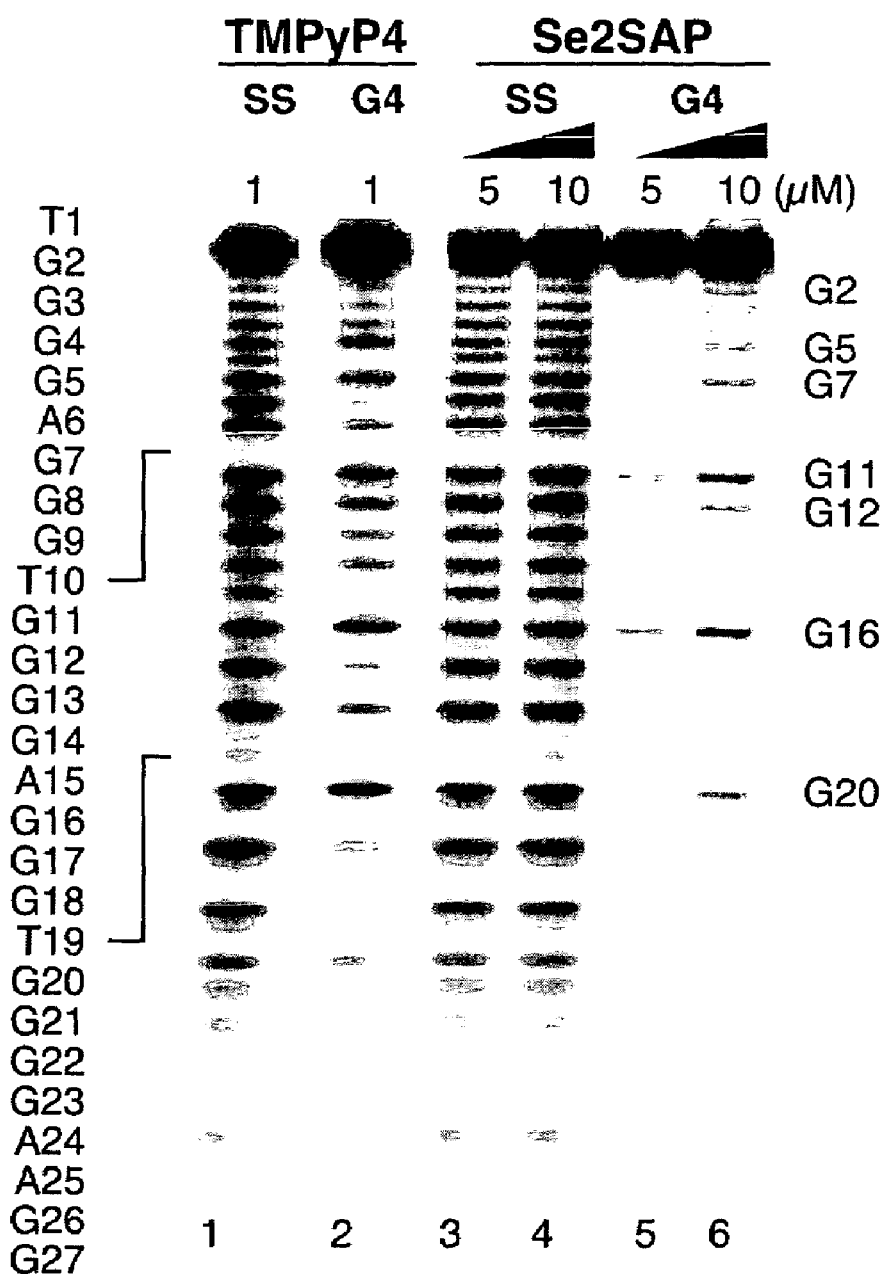
FIG. 7 shows similar results to those of FIG. 6 but compares TMPyP4 with Se2SAP.

In performing this test on the invention compound, Se2SAP, the non-photoactive nature of Se2SAP was demonstrated by the minimal cleavage by Se2SAP compared to TMPyP4 in the photoinduced cleavage of c-MYC G-quadruplex (FIG. 7). This is in accord with the lack of fluorescence by Se2SAP. The cleavage patterns for Se2SAP showed the similar mode of binding to that of TMPyP4 in the c-MYC G-quadruplex.

EXAMPLE 5

Cytotoxicity Tests

HeLa S3 (human cervical carcinoma metastasis were obtained from ATCC, and were cultured in Dulbecco's modification of Eagle's Medium (DMEM, Cellgro) with 10% FBS, 50 U/ml penicillin G sodium, 50 U/ml streptomycin sulfate. Adherent cells were grown to 80% confluency and passaged at 1:10 in the following fashion. The medium was aspirated by vacuum, and the cells were washed with 1×PBS (Cellgro). Sufficient trypsin (Gibco/BRL) was added to cover the cells, and cells were incubated at room temperature for approximately 3 min, or until cells detached from the flask with firm tapping. The trypsin was neutralized with an equal volume of culture medium, and the cells were counted using a haemocytometer and passaged at 1:10 into fresh medium. The remaining cells were then pelleted by centrifugation at 500× gravity (g), the supernatant was aspirated, and the pellet was washed in PBS, recentrifuged, and frozen at −80° C. for storage.

Figure 8:
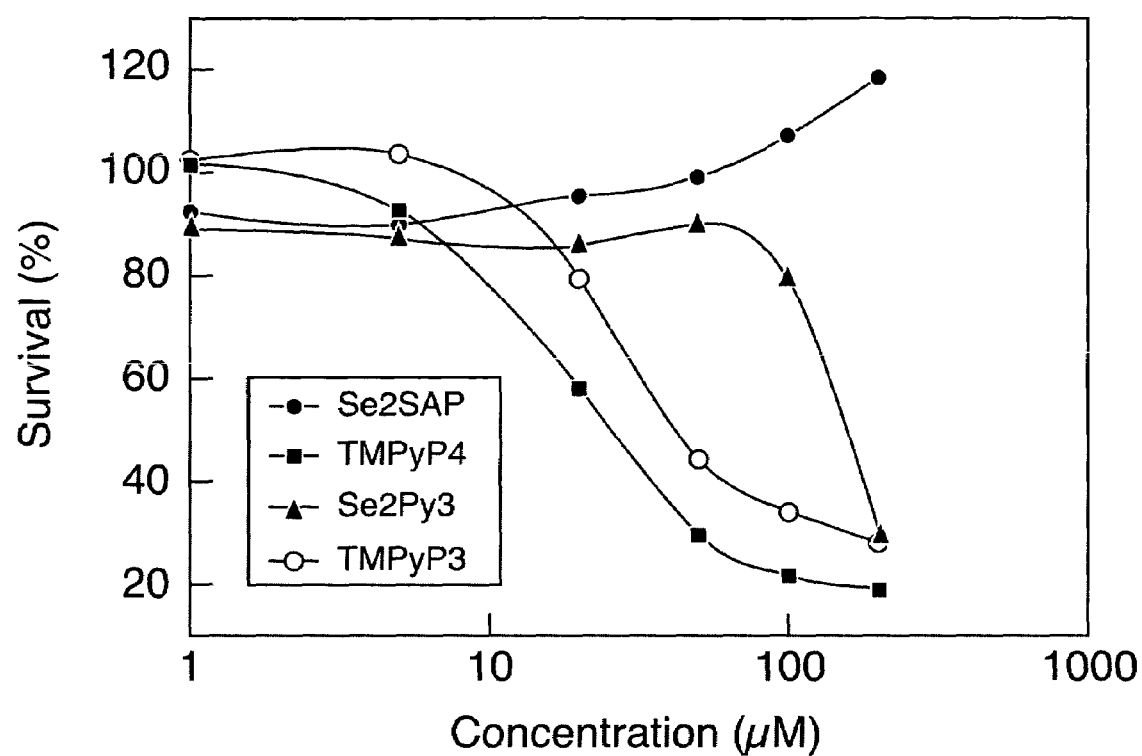
FIG. 8 is a graph of the percent survival of He La cells at various concentrations of the porphyrins and expanded porphyrins tested.

In vitro cytotoxicity assays were performed using the CellTiter 96 Non-Radioactive Cell Proliferation Assay (Promega Corp., Madison, Wis.). Cells were plated in 0.1 mL medium on day 0 in 96-well microtiter plates (Falcon, #3072). On day 1, 10 µL of serial dilutions of the test compound were added in replicates of 4 to the plates. After incubation for 4 days at 37° C. in a humidified incubator, 20 µL of a 20:1 mixture of 2 mg/mL MTS [3-(4,5-dimethyl-2-yl)-5-(3-carboxymethoxyphenyl)-2-(4-sulfophenyl)-2H-tetrazolium, inner salt] and an electron coupling reagent, phenazine methosulfate (0.92 mg/mL in DPBS), was added to each well and incubated for 4 h at 37° C. Absorbance was measured using a Wallac Victor Multilabel Counter (Perkin Elmer, Shelton, Conn.) at 490 nm. Data were expressed as the percentage of survival of control calculated from the absorbance corrected for background absorbance. The surviving fraction of cells was determined by dividing the mean absorbance values of the test agents by the mean absorbance values of untreated control. The results are shown in FIG. 8. While TMPyP4, TMPyP3 and Se2Py3 show cytotoxicities at $ED_{50}$ of 25.57, 43.44 and 151.51 µM respectively, Se2SAP is non cytotoxic even at 200 µM.

EXAMPLE 6

Effect on Transcription

In this example, the various porphyrins were tested for their effect on c-MYC RNA levels normalized to the levels of β-actin RNA production.

Se2Py3 and Se2SAP were tested at a variety of concentrations, ranging from 100 nM to 100 µM, to account for their G-quadruplex stabilizing activities. TMPyP4, at a concentration of 100 µM, was also included for comparison.

Cell cultures were permitted to reach ~50% confluency before test compound was added for 24 hour treatments. This was adjusted as necessary depending on treatment times. Test compounds were diluted in media in which the cells were normally cultured. Cells were washed once with PBS, and new media containing compound was added directly to the flask. Cells were harvested concurrently with untreated cells. Timepoints were collected in duplicate for each treatment.

RNA was extracted as follows: Cell pellets were lysed in Buffer RA I supplemented with 1% β-mercaptoethanol and RNA extracted according to the protocol included with the kit, and eluted in 50 µl of nuclease-free water included in the kit. RNA was quantitated by ultraviolet spectrophotometry, resuspended to a convenient concentration for downstream applications, and stored at −80° C.

Total RNA was used as a template for reverse transcription, using the following protocol: Each 20 µl reaction contained 1× Reaction buffer (Fermentas), 500 µM each of dCTP, dATP, dGTP, and dTTP (Fermentas), 0.5 µg Oligo $(dT)_{18}$ primer (Fermentas), 1 U M-MuLV Reverse Transcriptase (Fermentas), 20 U Ribonuclease Inhibitor (Fermentas), DEPC-$H_2O$, and 2 µg of total RNA. RNA, oligo $(dT)_{18}$, and DEPC-$H_2O$ were preheated to 70° C. for 5 minutes. Reaction buffer, ribonuclease inhibitor and deoxynucleotides were added, and the mixture was incubated at 37° C. for 5 minutes. Finally, reverse transcriptase was added, and the reaction was allowed to proceed for 1 hour at 37° C. The reaction was stopped by a 10 minute incubation at 72° C. All incubations were carried out in a DNA Engine Peltier Thermal Cycler (MJ Research). Reaction products were held at 4° C. and stored at −20° C.

Real-time PCR was performed using the QuantiTect SYBR Green PCR Kit (Qiagen). Briefly, each 25 µl reaction contained 12.5 µl of 2× reaction buffer, 0.5 µl of each mycRT primer (see Table 2.2) OR 1 µl of Actin Primer Pair (Ambion), 1 µl of cDNA, and 10.5 µl of distilled, deionized water.

Primer sequences were as follows:

```
MycRTfwd:  CTTGGCGGGAAAAAGAACGC

MycRTrev:  TATTCGCTCCGGATCTCCCT
```

The reactions were incubated in a DNA Engine Opticon Continuous Fluorescence Detector (MJ Research) as follows: 95° C., 14 min; (95° C., 1 min; 59° C., 1 min, 10 sec; 72° C., 1 min, 30 sec; plate read for fluorescence) 40×; 72° C., 10 min. A melting curve was then performed over the temperature range of 55° C. to 95° C., with a plate read at each 1° C. increment, to ensure that only a single PCR product had been produced in each well. Quantitation was performed using the integral Opticon software, and data are presented as -fold expression of c-MYC (normalized to β-actin) versus an untreated control.

Figure 9:
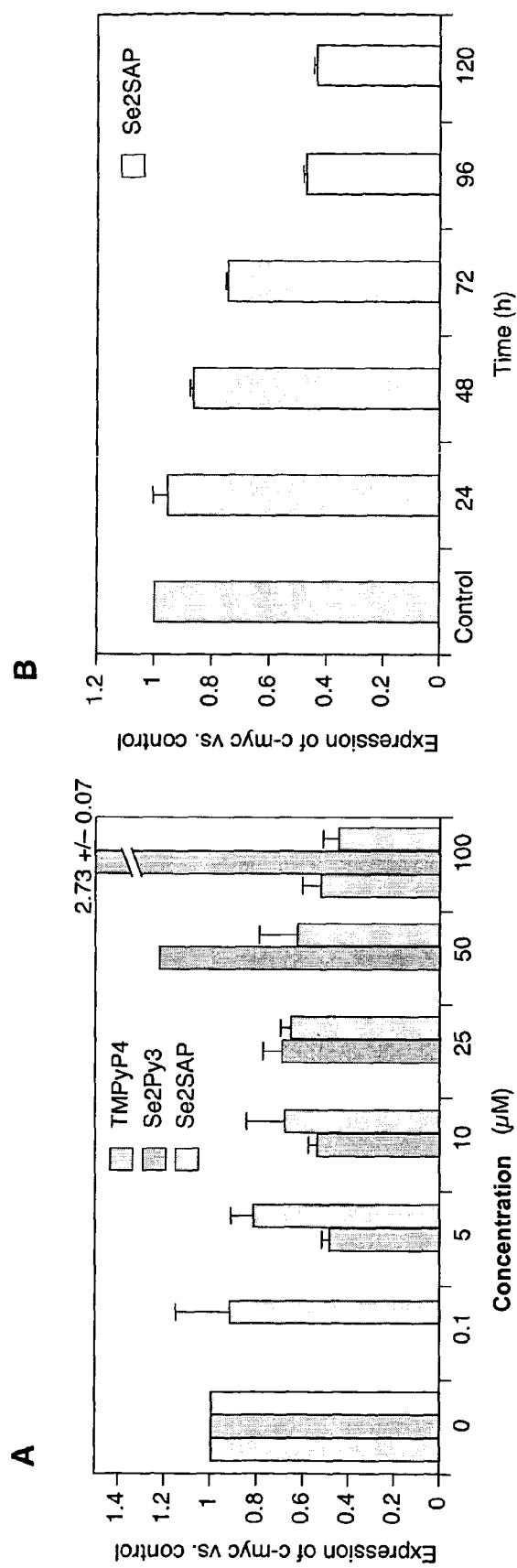
FIG. 9A is a graph showing the comparison of expression of c-MYC at various concentrations of the porphyrins and expanded porphyrins tested.
FIG. 9B shows the effect of Se2SAP on expression at various timepoints.

The results are shown in FIG. 9. In FIG. 9A HeLa $S_3$ cells were treated with the indicated concentrations of TMPyP4, Se2Py3, or Se2SAP, or an equal volume of water (control) for 24 h, and total RNA was extracted and subjected to reverse transcription followed by real-time PCR for c-MYC or β-actin. c-MYC expression was quantified and normalized to β-actin expression. The graph shows relative expression of c-MYC as compared to the control sample. In FIG. 9B, the time-dependent effect of Se2SAP on c-MYC expression is shown. HeLa $S_3$ cells were treated with 10 µM Se2SAP for the indicated times, and c-MYC expression was assayed as was done to obtain the results in FIG. 9A.

As shown in FIG. 9A, at 5 µM, the lowest concentration tested for Se2Py3, an effect similar to that of TMPyP4 was seen, implying that the selenaporphyrin is superior. However, this molecule also causes an increase in c-MYC expression as concentration increases, up to an apparent maximum of approximately 300%. However, as the dose of Se2SAP was increased the inhibitory effect of this molecule on c-MYC increased as well. Surprisingly, even at high (100 µM) concentration, the effect of Se2SAP comparable to TMPyP4.

EXAMPLE 7

Protocol for Determining c-MYC Expression in Tumor Tissue

Total RNA is extracted, subjected to poly(A)-specific reverse transcription to generate cDNA, and used as a template for specific PCR amplification of the c-MYC oncogene.

Biopsied cells are lysed in Buffer RLT from the RNeasy RNA Mini Extraction kit (QIAGen) and homogenized using a QIAShredder (QIAGen). RNA is extracted according to the manufacturer's protocol and eluted in distilled, deionized water with 0.1% diethyl pyrocarbonate (DEPC-$H_2O$; Sigma) to a final volume of 30 µl. RNA is quantitated by UV spectrophotometry and stored at −80° C.

Reverse transcription of the total RNA is as follows: Each 20-µl reaction contains 1× Omniscript RT buffer (QIAGen), 500 µM each of dCTP, dATP, dGTP, and dTTP (QIAGen), 1 µM Oligo dT primer (Ambion), 1 µM random decamer primers (Ambion), 1 unit of Omniscript reverse transcriptase (QIAGen), diethyl pyrocarbonate in water (DEPC-$H_2O$), and 2 µg of total RNA. Mixtures are incubated at 37° C. for 60 min for reverse transcription and then at 92° C. for 10 min to inactivate the enzyme. Both incubations are carried out in a DNA Engine Peltier Thermal Cycler (MJ Research). Reaction products are kept at 4° C. until ready to be used in the subsequent PCR.

PCR is performed as follows: Primers are:

```
c-MYC (upstream),     5'-AGAGAAGCTGGCCTCCTACC-3';

c-MYC (downstream),   5'-AGCTTTTGCTCCTCTGCTTG-3'.
```

Each 50-µl reaction contains 1×PCR buffer (Promega), 50 µM each of dCTP, dATP, dGTP, and dTTP (Promega), 0.5 µl β-actin primer pair (Ambion), 2.5 unit of Taq Polymerase (Promega), 0.5 µM c-MYC primer, 0.1% DEPC-$H_2O$, and 2 µl of the reverse transcriptase reaction. The product length is 2166 bp.

The invention claimed is:

1. An expanded porphyrin or a conjugate thereof comprising at least five pyrrole rings or pyrrole mimics wherein at least two NH or N moieties contained in said pyrrole rings or pyrrole mimics are replaced by S, Se and/or Te; said replacements occurring in non-adjacent pyrrole rings or pyrrole mimics;

wherein said expanded porphyrin is substituted with at least one $R^1$ moiety which is cationic under physiological conditions; and wherein said porphyrin may optionally be substituted by one or more non-interfering substituents and one or more carbons contained in a pyrrole ring may be replaced by O or S.

2. The expanded porphyrin or conjugate of claim 1, wherein the expanded porphyrin is of the formula

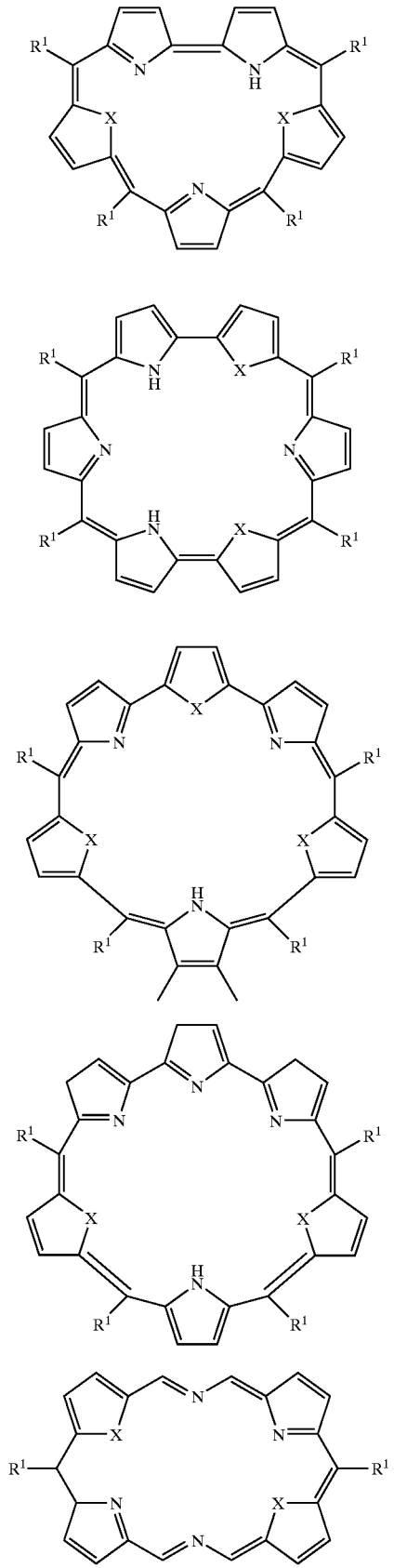

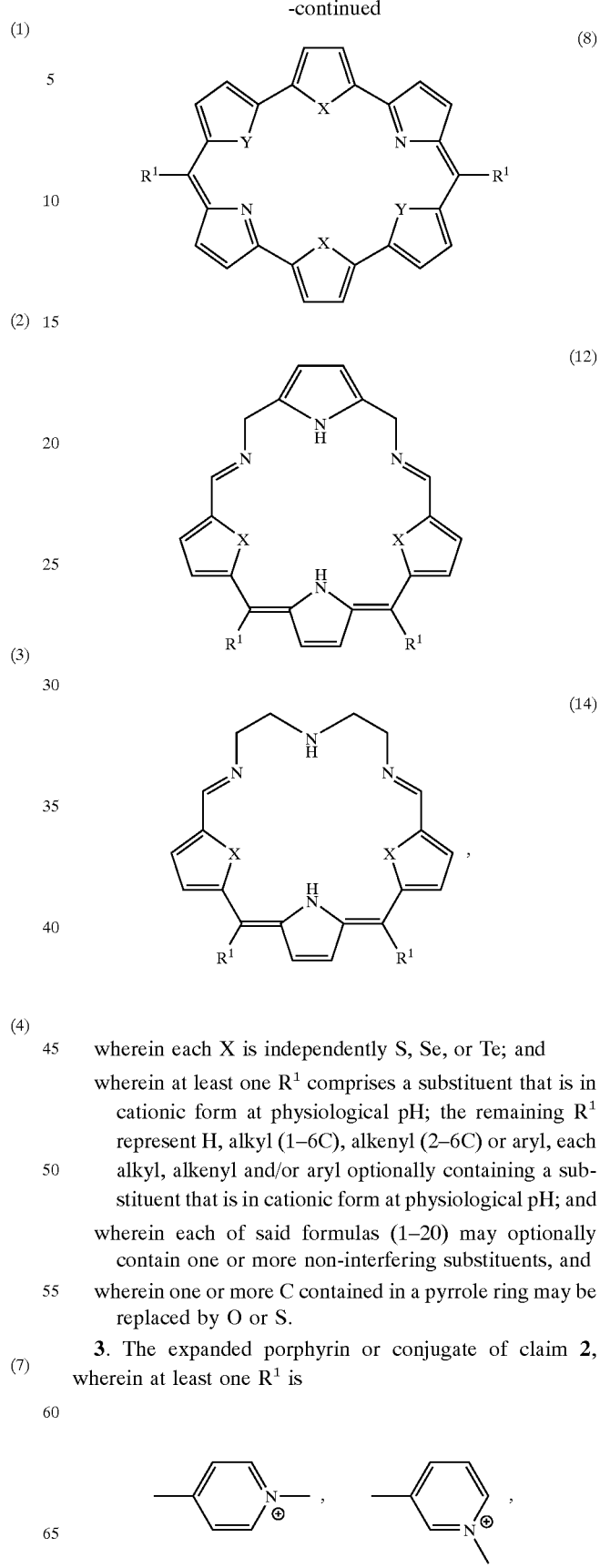

wherein each X is independently S, Se, or Te; and wherein at least one $R^1$ comprises a substituent that is in cationic form at physiological pH; the remaining $R^1$ represent H, alkyl (1–6C), alkenyl (2–6C) or aryl, each alkyl, alkenyl and/or aryl optionally containing a substituent that is in cationic form at physiological pH; and wherein each of said formulas (1–20) may optionally contain one or more non-interfering substituents, and wherein one or more C contained in a pyrrole ring may be replaced by O or S.

3. The expanded porphyrin or conjugate of claim 2, wherein at least one $R^1$ is -continued

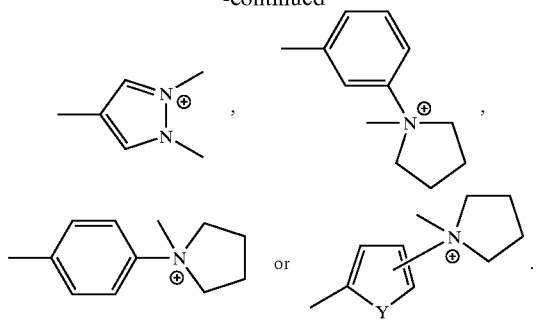

4. The expanded porphyrin or conjugate of claim 1 wherein the expanded porphyrin is Se2SAP.

5. A pharmaceutical composition for treating tumors which comprises as active ingredient the expanded porphyrin or conjugate of claim 1 in admixture with a physiologically acceptable excipient.

6. A method to treat tumors in a subject, which method comprises administering to a subject in need of such treatment an effective amount of the expanded porphyrin or conjugate of claim 1 or a pharmaceutical composition thereof.

* * * * *